US009670283B2

(12) United States Patent
Su

(10) Patent No.: US 9,670,283 B2
(45) Date of Patent: Jun. 6, 2017

(54) DEPLETION OF PLASMACYTOID DENDRITIC CELLS

(71) Applicant: The University of North Carolina at Chapel Hill, Chapel Hill, NC (US)

(72) Inventor: Lishan Su, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/092,275

(22) Filed: Apr. 6, 2016

(65) Prior Publication Data

US 2016/0280790 A1 Sep. 29, 2016

Related U.S. Application Data

(63) Continuation of application No. PCT/US2014/070521, filed on Dec. 16, 2014.

(60) Provisional application No. 61/916,322, filed on Dec. 16, 2013.

(51) Int. Cl.

*A61K 39/395* (2006.01)
*C07K 16/28* (2006.01)
*C12N 5/00* (2006.01)
*A61K 39/00* (2006.01)

(52) U.S. Cl.

CPC .... *C07K 16/2851* (2013.01); *A61K 39/39541* (2013.01); *C12N 5/0081* (2013.01); *A61K 2039/505* (2013.01); *C07K 2317/24* (2013.01); *C07K 2317/34* (2013.01); *C07K 2317/76* (2013.01)

(58) Field of Classification Search

None

See application file for complete search history.

(56) References Cited

U.S. PATENT DOCUMENTS 6,972,323 B1 12/2005 Serizawa et al.
7,888,481 B2 * 2/2011 Banchereau ......... C07K 16/249 424/130.1
8,022,188 B2 9/2011 Siegel et al.
2006/0228299 A1 10/2006 Thorpe et al.
2009/0324604 A1 12/2009 Liu et al.
2011/0268707 A1 11/2011 Gallagher et al.
2012/0087862 A1 4/2012 Hood et al.
2013/0315820 A1 11/2013 Fournier et al.

FOREIGN PATENT DOCUMENTS

EP 2286835 A1 2/2011
FR WO 2012080642 A1 * 6/2012 ......... C07K 16/2851
WO WO 91/09967 A1 7/1991
WO WO 01/36487 A2 5/2001

OTHER PUBLICATIONS

Swiecki et al., 2010, Immunity, vol. 33: 955-966.*
Hui et al., 2005, Alim. Pharm. Ther. vol. 22: 519-528.*
Blomberg et al. "Expression of the Markers BDCA-2 and BDCA-4 and Production of Interferon-α by Plasmacytoid Dendritic Cells in Systemic Lupus Erythematosus", *Arthritis & Rheumatism* 48(9):2524-2532 (2003).
Nestle et al. "Plasmacytoid predendritic cells initiate psoriasis through interferon-α production", *J. Exp. Med.* 202(1):135-143 (2005).
Swiecki et al. "Unraveling the functions of plasmacytoid dendritic cells during viral infections, autoimmunity, and tolerance", *Immunol Rev.* 234(1):142-162 (2010).
Database GenBank: CAA01595.1, Nov. 16, 2004.
Database GenBank: CAA01594.1, Nov. 29, 2004.
Database GenBank: AEP59406.1, Sep. 30, 2011.
Database GenBank: ABC16461.1, Dec. 8, 2005.
Notification of Transmittal of the International Search Report and the Written Opinion of the International Searching Authority, or the Declaration corresponding to International Application No. PCT/US2014/070521 mailed Apr. 23, 2015.
Notification Concerning Transmittal of International Preliminary Report on Patentability corresponding to International Application No. PCT/US2014/070521 mailed Jun. 30, 2016.
U.S. Appl. No. 15/442,157, filed Feb. 24, 2017; Office Action issued Mar. 31, 2017.

* cited by examiner

*Primary Examiner* — Amy Juedes
(74) *Attorney, Agent, or Firm* — Myers Bigel, P.A.

(57) ABSTRACT

The present invention relates to antibodies targeted to BDCA2 that deplete plasmacytoid dendritic cells (pDC) and methods of using the antibodies to treat disorders associated with pDC.

11 Claims, 28 Drawing Sheets

FIGS. 7a-7c
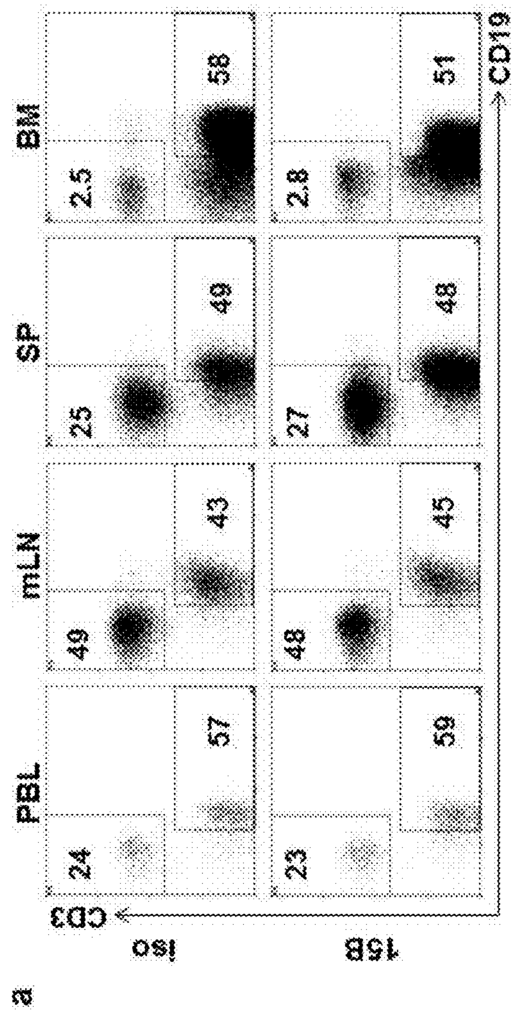
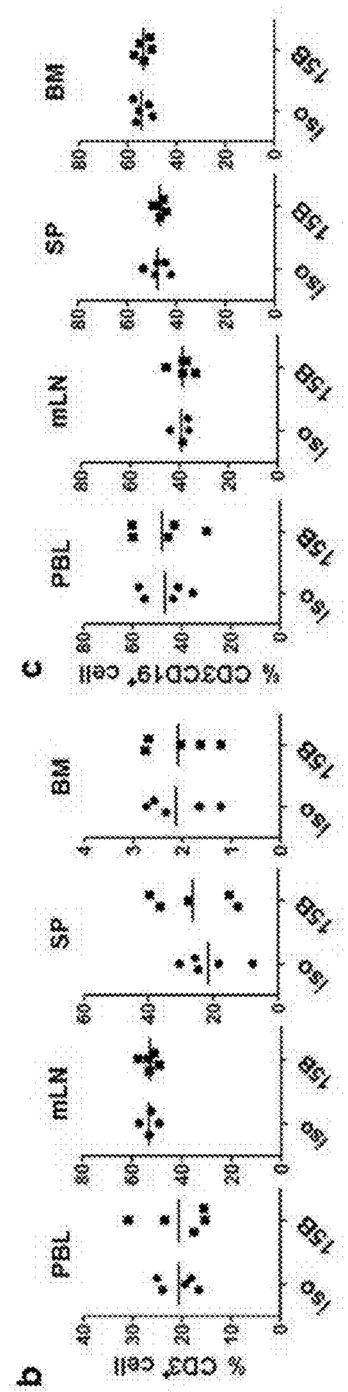

a
R3A
mock
iso
15B
PBL
SP
CD38
HLA-DR
b
%HLA-DR+CD38+ CD8 T cell
c
JR-CSF
d

FIG. 18

Signal peptide

```
    M   G   W   N   W   I   F   I   L   I   L   S   V   T   T   G   V   H   S   E
  1 ATG GGA TGG AAC TGG ATC TTT ATT TTA ATC CTG TCA GTA ACT ACA GGT GTC CAC TCT GAG

    V   Q   L   Q   Q   S   G   P   E   L   V   K   P   G   A   S   V   K   I   S
 61 GTC CAA CTG CAG CAG TCT GGA CCT GAG CTG GTG AAG CCT GGG GCT TCA GTG AAG ATA TCC

    C   K   A   S   G   Y   S   F   T   V   Y   Y   M   H   W   V   K   Q   S   P
121 TGC AAG GCT TCT GGT TAC TCA TTC ACT GTC TAC TAC ATG CAC TGG GTG AAG CAA AGT CCT

    E   N   S   L   E   W   I   G   E   I   N   P   S   T   G   G   T   S   Y   N
181 GAA AAT AGT CTT GAG TGG ATT GGA GAG ATT AAT CCT AGC ACT GGG GGT ACT AGC TAC AAC

    Q   K   F   K   G   K   A   T   L   T   V   D   E   S   S   S   T   A   Y   M
241 CAG AAG TTC AAG GGC AAG GCC ACA TTA ACT GTA GAT GAA TCC TCC AGC ACA GCC TAC ATG

    Q   L   K   S   L   T   S   E   E   S   A   V   Y   Y   C   T   T   P   Y   Y
301 CAG CTC AAG AGC CTG ACA TCT GAA GAG TCT GCA GTC TAT TAC TGT ACA ACC CCC TAC TAT

    R   Y   E   G   D   W   Y   F   D   V   W   G   A   G   T   T   V   T   V   S
361 AGG TAC GAG GGG GAC TGG TAC TTC GAT GTC TGG GGC GCA GGG ACC ACG GTC ACC GTC TCC

    S   A   K   T   T   A   P   S   V   Y   P   L   A   P   V   C   G   D   T   T
421 TCA GCT AAA ACA ACA GCC CCA TCG GTC TAT CCA CTG GCC CCT GTG TGT GGA GAT ACA ACT

    G   S   S   V   T   L   G   C   L   V   K   G   Y   F   P   E   P   V   T   L
481 GGC TCC TCG GTG ACT CTA GGA TGC CTG GTC AAG GGT TAT TTC CCT GAG CCA GTG ACC TTG

    T   W   N   S   G   S   L   S   S   G   V   H   T   F   P   A   V   L   Q   S
541 ACC TGG AAC TCT GGA TCC CTG TCC AGT GGT GTG CAC ACC TTC CCA GCT GTC CTG CAG TCT

    D   L   Y   T   L   S   S   S   V   T   V   T   S   S   T   W   P   S   Q   S
601 GAC CTC TAC ACC CTC AGC AGC TCA GTG ACT GTA ACC TCG AGC ACC TGG CCC AGC CAG TCC

    I   T   C   N   V   A   H   P   A   S   S   T   K   V   D   K   K   I   E   P
661 ATC ACC TGC AAT GTG GCC CAC CCG GCA AGC AGC ACC AAG GTG GAC AAG AAA ATT GAG CCC

    R   G   P   T   I   K   P   C   P   P   C   K   C   P   A   P   N   L   L   G
721 AGA GGG CCC ACA ATC AAG CCC TGT CCT CCA TGC AAA TGC CCA GCA CCT AAC CTC TTG GGT

    G   P   S   V   F   I   F   P   P   K   I   K   D   V   L   M   I   S   L   S
781 GGA CCA TCC GTC TTC ATC TTC CCT CCA AAG ATC AAG GAT GTA CTC ATG ATC TCC CTG AGC
```

FIG. 18 (Continued)

```
     P   I   V   T   C   V   V   V   D   V   S   E   D   D   P   D   V   Q   I   S
841  CCC ATA GTC ACA TGT GTG GTG GTG GAT GTG AGC GAG GAT GAC CCA GAT GTC CAG ATC AGC

     W   F   V   N   N   V   E   V   H   T   A   Q   T   Q   T   H   R   E   D   Y
901  TGG TTT GTG AAC AAC GTG GAA GTA CAC ACA GCT CAG ACA CAA ACC CAT AGA GAG GAT TAC

     N   S   T   L   R   V   V   S   A   L   P   I   Q   H   Q   D   W   M   S   G
961  AAC AGT ACT CTC CGG GTG GTC AGT GCC CTC CCC ATC CAG CAC CAG GAC TGG ATG AGT GGC

     K   E   F   K   C   K   V   N   N   K   D   L   P   A   P   I   E   R   T   I
1021 AAG GAG TTC AAA TGC AAG GTC AAC AAC AAA GAC CTC CCA GCG CCC ATC GAG AGA ACC ATC

     S   K   P   K   G   S   V   R   A   P   Q   V   Y   V   L   P   P   P   E   E
1081 TCA AAA CCC AAA GGG TCA GTA AGA GCT CCA CAG GTA TAT GTC TTG CCT CCA CCA GAA GAA

     E   M   T   K   K   Q   V   T   L   T   C   M   V   T   D   F   M   P   E   D
1141 GAG ATG ACT AAG AAA CAG GTC ACT CTG ACC TGC ATG GTC ACA GAC TTC ATG CCT GAA GAC

     I   Y   V   E   W   T   N   N   G   K   T   E   L   N   Y   K   N   T   E   P
1201 ATT TAC GTG GAG TGG ACC AAC AAC GGG AAA ACA GAG CTA AAC TAC AAG AAC ACT GAA CCA

     V   L   D   S   D   G   S   Y   F   M   Y   S   K   L   R   V   E   K   K   N
1261 GTC CTG GAC TCT GAT GGT TCT TAC TTC ATG TAC AGC AAG CTG AGA GTG GAA AAG AAG AAC

     W   V   E   R   N   S   Y   S   C   S   V   V   H   E   G   L   H   N   H   H
1321 TGG GTG GAA AGA AAT AGC TAC TCC TGT TCA GTG GTC CAC GAG GGT CTG CAC AAT CAC CAC

     T   T   K   S   F   S   R   T   P   G   K   *
1381 ACG ACT AAG AGC TTC TCC CGG ACT CCG GGT AAA TAA
```

FIG. 19

```
                                Signal peptide
     M   H   F   Q   V   Q   I   F   S   F   L   L   I   S   A   S   V   I   M   S
   1 ATG CAT TTT CAA GTG CAG ATT TTC AGC TTC CTG CTA ATC AGT GCC TCA GTC ATA ATG TCC

     R   G   Q   I   V   L   T   Q   S   P   A   I   M   S   A   S   P   G   E   K
  61 AGA GGA CAA ATT GTT CTC ACC CAG TCT CCA GCA ATC ATG TCT GCA TCT CCA GGG GAG AAG

     V   T   I   T   C   S   A   S   S   S   V   S   Y   M   H   W   F   Q   Q   K
 121 GTC ACC ATA ACC TGC AGT GCC AGC TCA AGT GTA AGT TAC ATG CAC TGG TTC CAG CAG AAG

     P   G   T   S   P   K   L   W   I   Y   S   T   S   N   L   A   S   G   V   P
 181 CCA GGC ACT TCT CCC AAA CTC TGG ATT TAT AGC ACA TCC AAC CTG GCT TCT GGA GTC CCT

     A   R   F   S   G   S   G   S   G   T   S   Y   S   L   T   I   S   R   M   E
 241 GCT CGC TTC AGT GGC AGT GGA TCT GGG ACC TCT TAC TCT CTC ACA ATC AGC CGA ATG GAG

     A   E   D   A   A   T   Y   Y   C   H   Q   R   S   S   Y   P   R   T   F   G
 301 GCT GAA GAT GCT GCC ACT TAT TAC TGC CAC CAA AGG AGT AGT TAC CCA CGG ACG TTC GGT

     G   G   T   K   L   E   I   R   R   A   D   A   A   P   T   V   S   I   F   P
 361 GGA GGC ACC AAG CTG GAA ATC AGA CGG GCT GAT GCT GCA CCA ACT GTA TCC ATC TTC CCA

     P   S   S   E   Q   L   T   S   G   G   A   S   V   V   C   F   L   N   N   F
 421 CCA TCC AGT GAG CAG TTA ACA TCT GGA GGT GCC TCA GTC GTG TGC TTC TTG AAC AAC TTC

     Y   P   K   D   I   N   V   K   W   K   I   D   G   S   E   R   Q   N   G   V
 481 TAC CCC AAA GAC ATC AAT GTC AAG TGG AAG ATT GAT GGC AGT GAA CGA CAA AAT GGC GTC

     L   N   S   W   T   D   Q   D   S   K   D   S   T   Y   S   M   S   S   T   L
 541 CTG AAC AGT TGG ACT GAT CAG GAC AGC AAA GAC AGC ACC TAC AGC ATG AGC AGC ACC CTC

     T   L   T   K   D   E   Y   E   R   H   N   S   Y   T   C   E   A   T   H   K
 601 ACG TTG ACC AAG GAC GAG TAT GAA CGA CAT AAC AGC TAT ACC TGT GAG GCC ACT CAC AAG

     T   S   T   S   P   I   V   K   S   F   N   R   N   E   C   *
 661 ACA TCA ACT TCA CCC ATT GTC AAG AGC TTC AAC AGG AAT GAG TGT TAG
```

FIG. 21

Signal Peptide

```
      M   N   F   G   F   S   L   I   F   L   V   L   V   L   K   G   V   Q   C   E
  1  ATG AAC TTC GGG TTC AGC TTG ATT TTC CTT GTC CTT GTT TTA AAA GGT GTC CAG TGT GAA

      V   K   L   V   E   S   G   G   G   L   V   K   P   G   G   S   L   K   L   S
 61  GTG AAG CTG GTG GAG TCT GGG GGA GGC TTA GTG AAG CCT GGA GGG TCC CTG AAA CTC TCC

      C   A   A   S   G   F   T   F   S   T   M   S   W   V   R   Q   T   P   E   K
121  TGT GCA GCC TCT GGA TTC ACT TTC AGT ACC ATG TCT TGG GTT CGC CAG ACT CCA GAG AAG

      R   L   E   W   V   A   S   I   S   S   G   G   S   T   Y   Y   P   D   S   V
181  AGG CTG GAG TGG GTC GCA TCC ATT AGT AGT GGT GGT AGT ACT TAC TAT CCA GAC AGT GTG

      K   G   R   F   T   I   S   R   D   N   A   R   N   I   L   Y   L   Q   M   S
241  AAG GGC CGA TTC ACC ATC TCC AGA GAT AAT GCC AGG AAC ATC CTG TAC CTG CAA ATG AGC

      S   L   R   S   E   D   T   A   M   Y   Y   C   A   R   P   S   Y   D   G   Y
301  AGT CTG AGG TCT GAG GAC ACG GCC ATG TAT TAC TGT GCA AGA CCC TCT TAT GAT GGT TAC

      S   S   W   F   A   Y   W   G   Q   G   T   L   V   T   V   S   A   A   K   T
361  TCC TCC TGG TTT GCT TAC TGG GGC CAA GGG ACT CTG GTC ACT GTC TCT GCA GCC AAA ACA

      T   A   P   S   V   Y   P   L   A   P   V   C   G   D   T   T   G   S   S   V
421  ACA GCC CCA TCG GTC TAT CCA CTG GCC CCT GTG TGT GGA GAT ACA ACT GGC TCC TCG GTG

      T   L   G   C   L   V   K   G   Y   F   P   E   P   V   T   L   T   W   N   S
481  ACT CTA GGA TGC CTG GTC AAG GGT TAT TTC CCT GAG CCA GTG ACC TTG ACC TGG AAC TCT

      G   S   L   S   S   G   V   H   T   F   P   A   V   L   Q   S   D   L   Y   T
541  GGA TCC CTG TCC AGT GGT GTG CAC ACC TTC CCA GCT GTC CTG CAG TCT GAC CTC TAC ACC
```

FIG. 21 (Continued)

```
      L   S   S   S   V   T   V   T   S   S   T   W   P   S   Q   S   I   T   C   N
601   CTC AGC AGC TCA GTG ACT GTA ACC TCG AGC ACC TGG CCC AGC CAG TCC ATC ACC TGC AAT

      V   A   H   P   A   S   S   T   K   V   D   K   K   I   E   P   R   G   P   T
661   GTG GCC CAC CCG GCA AGC AGC ACC AAG GTG GAC AAG AAA ATT GAG CCC AGA GGG CCC ACA

      I   K   P   C   P   P   C   K   C   P   A   P   N   L   L   G   G   P   S   V
721   ATC AAG CCC TGT CCT CCA TGC AAA TGC CCA GCA CCT AAC CTC TTG GGT GGA CCA TCC GTC

      F   I   F   P   P   K   I   K   D   V   L   M   I   S   L   S   P   I   V   T
781   TTC ATC TTC CCT CCA AAG ATC AAG GAT GTA CTC ATG ATC TCC CTG AGC CCC ATA GTC ACA

      C   V   V   V   D   V   S   E   D   D   P   D   V   Q   I   S   W   F   V   N
841   TGT GTG GTG GTG GAT GTG AGC GAG GAT GAC CCA GAT GTC CAG ATC AGC TGG TTT GTG AAC

      N   V   E   V   H   T   A   Q   T   Q   T   H   R   E   D   Y   N   S   T   L
901   AAC GTG GAA GTA CAC ACA GCT CAG ACA CAA ACC CAT AGA GAG GAT TAC AAC AGT ACT CTC

      R   V   V   S   A   L   P   I   Q   H   Q   D   W   M   S   G   K   E   F   K
961   CGG GTG GTC AGT GCC CTC CCC ATC CAG CAC CAG GAC TGG ATG AGT GGC AAG GAG TTC AAA

      C   K   V   N   N   K   D   L   P   A   P   I   E   R   T   I   S   K   P   K
1021  TGC AAG GTC AAC AAC AAA GAC CTC CCA GCG CCC ATC GAG AGA ACC ATC TCA AAA CCC AAA

      G   S   V   R   A   P   Q   V   Y   V   L   P   P   P   E   E   E   M   T   K
1081  GGG TCA GTA AGA GCT CCA CAG GTA TAT GTC TTG CCT CCA CCA GAA GAA GAG ATG ACT AAG

      K   Q   V   T   L   T   C   M   V   T   D   F   M   P   E   D   I   Y   V   E
1141  AAA CAG GTC ACT CTG ACC TGC ATG GTC ACA GAC TTC ATG CCT GAA GAC ATT TAC GTG GAG
```

FIG. 21 (Continued)

```
      W   T   N   N   G   K   T   E   L   N   Y   K   N   T   E   P   V   L   D   S
1201  TGG ACC AAC AAC GGG AAA ACA GAG CTA AAC TAC AAG AAC ACT GAA CCA GTC CTG GAC TCT

      D   G   S   Y   F   M   Y   S   K   L   R   V   E   K   K   N   W   V   E   R
1261  GAT GGT TCT TAC TTC ATG TAC AGC AAG CTG AGA GTG GAA AAG AAG AAC TGG GTG GAA AGA

      N   S   Y   S   C   S   V   V   H   E   G   L   H   N   H   H   T   T   K   S
1321  AAT AGC TAC TCC TGT TCA GTG GTC CAC GAG GGT CTG CAC AAT CAC CAC ACG ACT AAG AGC

      F   S   R   T   P   G   K   *
1381  TTC TCC CGG ACT CCG GGT AAA TAA
```

FIG. 22

Signal Peptide

```
      M   E   T   D   T   I   L   L   W   V   L   L   L   W   V   P   G   S   T   G
  1   ATG GAG ACA GAC ACA ATC CTG CTA TGG GTG CTG CTG CTC TGG GTT CCA GGC TCC ACT GGT

      D   I   V   L   T   Q   S   P   A   S   L   A   V   S   L   G   Q   R   A   T
 61   GAC ATT GTG CTG ACC CAA TCT CCA GCT TCT TTG GCT GTG TCT CTA GGG CAG AGG GCC ACC

      I   S   C   K   A   S   Q   S   V   D   Y   D   G   D   G   F   M   N   W   Y
121   ATC TCC TGC AAG GCC AGC CAA AGT GTT GAT TAT GAT GGT GAT GGT TTT ATG AAC TGG TAC

      Q   Q   K   P   G   Q   P   P   K   L   L   I   Y   T   A   S   N   L   E   S
181   CAA CAG AAA CCA GGA CAG CCA CCC AAA CTC CTC ATC TAT ACT GCA TCC AAT CTA GAA TCT

      G   I   P   A   R   F   S   G   S   G   S   G   T   D   F   T   L   N   I   H
241   GGG ATC CCA GCC AGG TTT AGT GGC AGT GGG TCT GGG ACA GAC TTC ACC CTC AAC ATC CAT

      P   V   E   E   E   D   A   A   T   Y   Y   C   Q   Q   S   N   E   D   P   W
301   CCT GTG GAG GAG GAG GAT GCT GCA ACC TAT TAC TGT CAG CAA AGT AAT GAG GAT CCG TGG

      T   F   G   G   G   T   K   L   E   I   K   R   A   D   A   A   P   T   V   S
361   ACG TTC GGT GGA GGC ACC AAG CTG GAA ATC AAA CGG GCT GAT GCT GCA CCA ACT GTA TCC

      I   F   P   P   S   S   E   Q   L   T   S   G   G   A   S   V   V   C   F   L
421   ATC TTC CCA CCA TCC AGT GAG CAG TTA ACA TCT GGA GGT GCC TCA GTC GTG TGC TTC TTG

      N   N   F   Y   P   K   D   I   N   V   K   W   K   I   D   G   S   E   R   Q
481   AAC AAC TTC TAC CCC AAA GAC ATC AAT GTC AAG TGG AAG ATT GAT GGC AGT GAA CGA CAA
```

FIG. 22 (Continued)

```
     N   G   V   L   N   S   W   T   D   Q   D   S   K   D   S   T   Y   S   M   S
541  AAT GGC GTC CTG AAC AGT TGG ACT GAT CAG GAC AGC AAA GAC AGC ACC TAC AGC ATG AGC

     S   T   L   T   L   T   K   D   E   Y   E   R   H   N   S   Y   T   C   E   A
601  AGC ACC CTC ACG TTG ACC AAG GAC GAG TAT GAA CGA CAT AAC AGC TAT ACC TGT GAG GCC

     T   H   K   T   S   T   S   P   I   V   K   S   F   N   R   N   E   C   *
661  ACT CAC AAG ACA TCA ACT TCA CCC ATT GTC AAG AGC TTC AAC AGG AAT GAG TGT TAG
```

DEPLETION OF PLASMACYTOID DENDRITIC CELLS

RELATED APPLICATIONS

This application is a continuation of International Application No. PCT/US2014/070521, filed Dec. 16, 2014 which claims the benefit of U.S. Provisional Application No. 61/916,322, filed Dec. 16, 2013. The entire contents of this application is fully incorporated herein by reference.

STATEMENT OF FEDERAL SUPPORT

This invention was made with government support under Grant No. AI077454 awarded by the National Institutes of Health. The government has certain rights in this invention.

STATEMENT REGARDING ELECTRONIC FILING OF A SEQUENCE LISTING

A Sequence Listing in ASCII text format, submitted under 37 C.F.R. §1.821, entitled 5470-680_ST25.txt, 34,663 bytes in size, generated on Apr. 4, 2016 and filed via EFS-Web, is provided in lieu of a paper copy. The Sequence Listing is incorporated herein by reference into the specification for its disclosures.

FIELD OF THE INVENTION

The present invention relates to antibodies targeted to BDCA2 that deplete plasmacytoid dendritic cells (pDC) and methods of using the antibodies to treat disorders associated with pDC.

BACKGROUND OF THE INVENTION

Plasmacytoid dendritic cells (pDC) are potent type I interferon (IFN-I) producing cells (Siegal et al., *Science* 284:1835 (1999)) and involved in controlling various viral infections (Cervantes-Barragan et al., *Proc. Nal. Acad. Sci. USA* 109:3012 (2012); Takagi et al., *Immunity* 35:958 (2011); Liu, *Annu. Rev. Immunol.* 23:275 (2005); Swiecki et al., *Immunity* 33:955 (2010)). However, the contribution of pDC in human immunodeficiency virus-1 (HIV-1) infection and pathogenesis remains controversial. On one hand, pDC have been shown to inhibit HIV-1 replication through IFN-1 production (Yonezawa et al., *J. Virol.* 77:3777 (2003); Fong et al., *J. Virol.* 76:11033 (2002); Gurney et al., *J. Immunol.* 173:7269 (2004)). Moreover, the numerical and functional decline of pDC in HIV-1 infected patients correlates with opportunistic infection independent of $CD4^+$ T-cell counts (Siegal et al., *J. Clin. Invest.* 78:115 (1986); Feldman et al., *Clin. Immunol.* 101:201 (2001); Lichtner et al., *Curr. HIV Res.* 6:19 (2008)). On the other hand, pDC may contribute to HIV immunopathogenesis. The sustained pDC activation and IFN-I production in HIV-1 infected patients does not correlate with viral control but is predictive of disease progression (Buimovici-Klein et al., *Lancet* 2:344 (1983); Buimovici-Klein et al., *AIDS Res.* 2:99-108 (1986); Meier et al., *Nature Medicine* 15:955 (2009)). Additionally, pDC are activated during the acute phase of simian immunodeficiency virus (SN) infection in both pathogenic Asian monkeys (Rhesus and cynomolgus macaques) and non-pathogenic African monkeys (Sooty mangabeys and African green monkeys). However, pDC activation is rapidly controlled in the nonpathogenic SIV infection, whereas its activation and IFN-I production are sustained during pathogenic infection in Asian monkey (Lederer et al., *PLoS Pathogens* 5:e1000296 (2009); Bosinger et al., *J. Clin. Invest.* 119:3556 (2009); Jacquelin et al., *J. Clin. Invest.* 119:3544 (2009); Harris et al., *J. Virol.* 84:7886 (2010); Campillo-Gimenez et al., *J. Virol.* 84:1838 (2010)). Thus, the interaction between HIV and pDCs is unclear.

The present invention addresses previous shortcomings in the art by providing antibodies that deplete pDC in a subject and treat disorders associated with pDC.

SUMMARY OF THE INVENTION

The present invention is based, in part, on the identification of antibodies that specifically bind to BDCA2 (blood dendritic cell antigen-2) and deplete pDC (e.g., reduces the number of pDC) when administered to a subject. The invention is based further on the use of these antibodies to deplete pDC in a subject and to treat disorders associated with pDC in a subject.

Accordingly, in one aspect, the invention relates to methods of depleting pDC in a subject, comprising delivering to the subject an antibody or a fragment thereof that specifically binds to BDCA2 and depletes pDC, thereby depleting pDC.

In another aspect, the invention relates to methods of treating a disorder associated with pDC in a subject, comprising delivering to the subject an antibody or a fragment thereof that specifically binds to BDCA2 and depletes pDC, thereby treating the disorder.

In an additional aspect, the invention relates to the use of an antibody or a fragment thereof that specifically binds to BDCA2 and depletes pDC in the preparation of a medicament for treating a disorder associated with pDC.

In another embodiment, the invention relates to the use of antibody or a fragment thereof that specifically binds to BDCA2 and depletes pXDC for treating a disorder associated with pDC.

In a further aspect, the invention relates to antibodies or fragments thereof that specifically bind to BDCA2 and deplete pDC when administered to a subject.

These and other aspects of the invention are set forth in more detail in the description of the invention below.

BRIEF DESCRIPTION OF THE DRAWINGS

FIGS. 3*a*-3*e* show CD8 T cell activation in acute R3A infection and chronic JR-CSF infection in DKO-hu mice. (a)

Representative FACS plots for the percentages of HLA-DR+CD38+CD8 T cells in peripheral blood and spleen in R3A-infected mice at 3 weeks post-infection. (b) Representative FACS plots for the percentages of HLA-DR+CD38+CD8 T cells in peripheral blood and spleen in JR-CSF-infected mice at 18 weeks post-infection. (c) Summarized data for supplementary FIG. 2$b$. mock n=4; JR-CSF n=10. All bars in dot graphs indicate median value. ** indicate p<0.01.

Figures 3A, 3B, 3C:
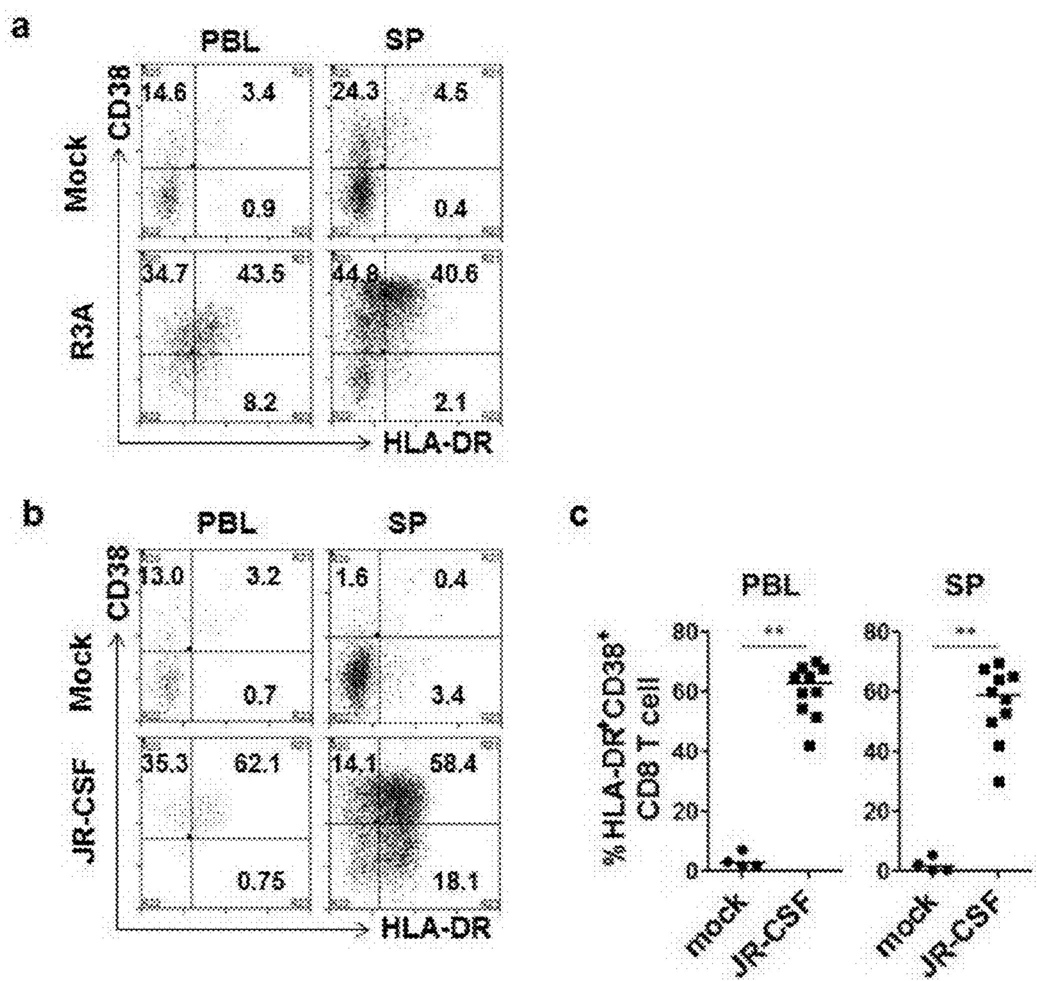
Figures 4A, 4B, 4C:
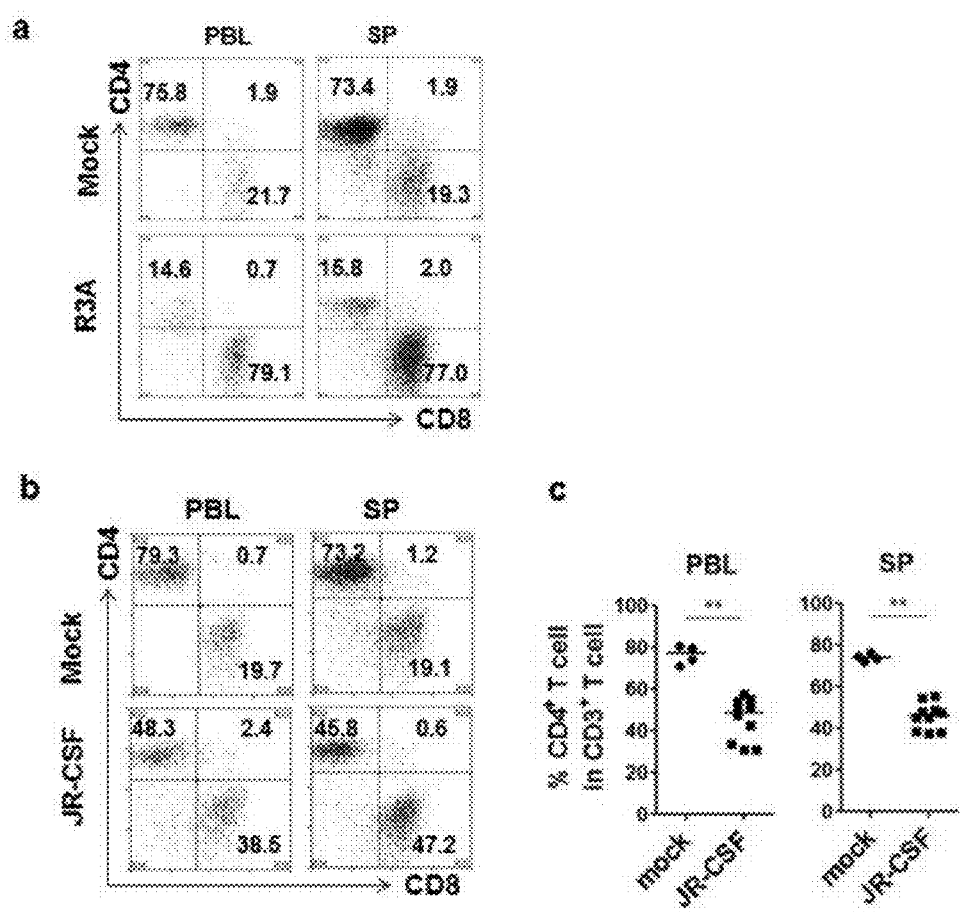

FIGS. 4$a$-4$c$ show CD4 T cell depletion in acute R3A infection and chronic JR-CSF infection in DKO-hu mice. (a) Representative FACS plots for the percentages of CD4 T cells (CD8-CD4) in peripheral blood and spleen in R3A-infected mice at 3 weeks post-infection. (b) Representative FACS plots for the percentages of CD4 T cells (CD8-CD4+) in peripheral blood and spleen in R3A-infected mice at 18 weeks post-infection. (c) Summarized data for supplementary FIG. 3$b$. mock n=4; JR-CSF n=10. All bars in dot graphs indicate median value. ** indicate p<0.01.

FIGS. 5$a$-5$c$ show type I IFN response and HIV pathogenesis in R5-tropic JR-CSF-infected humanized mice terminated at 3 weeks post-infection. (a) Comparison of absolute CD4 T-cell, CD8 T-cell and human CD45+ cell numbers in spleen from uninfected control mice (n=4) and JR-CSF-infected mice (n=−10). (b) The production of IFN-α2 in plasma from uninfected (n=3) and infected (n=3) humanized mice measured by luminex. (c) The relative level of Mx1 and TRIM22 gene expression in human CD45+ cells isolated from spleens. All bars in dot graphs indicate median value. Error bars indicate standard deviations (SD). * and ** indicate p<0.05 and p<0.01, respectively.

FIGS. 6$a$-6$b$ show depletion of pDC mediated by 15B in DKO-hu mice. (a-b) Humanized mice were treated with either 15B or isotype control (iso) antibody, pDC (CD4+CD123+) percentage of total human leukocytes (CD45+) were analyzed by FACS. (a) Representative FACS plots and summarized data show relative pDC frequencies before and after antibody treatment in peripheral blood (n=7). (b) Representative FACS plots and summarized data show pDC depletion by 15B in mesenteric lymph nodes (mLN, isotype n=4; 15B n=5) and spleen (SP, isotype n=4; 15B n=5). All bars in dot graphs indicate median value. Error bars indicate standard deviations (SD). * and ** indicate p<0.05 and p<0.01, respectively.

FIGS. 7$a$-7$c$ show specific depletion of pDCs induced by 15B in different lymphoid organs in DKO-hu mice. (a) Representative FACS plots show percentages of CD3+CD19− cell and CD3−CD19+ cell in huCD45+ cells. (b-c) Summarized data for FIG. 7$a$. All bars in dot graphs indicate median value.

Figures 8A, 8B:
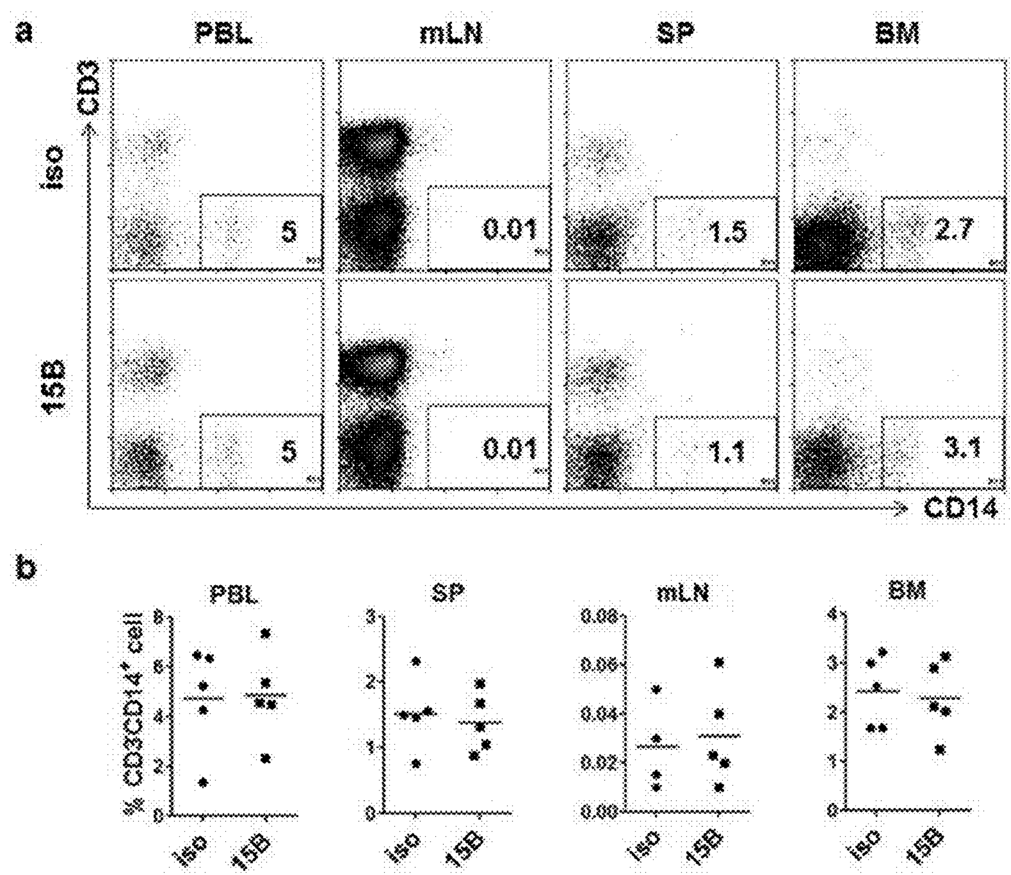

FIGS. 8$a$-8$b$ show specific depletion of pDCs induced by 15B in different lymphoid organs in DKO-hu mice. (a) Representative FACS plots show percentages of CD3-CD14+ cell in huCD45+ cells. (b) Summarized data for FIG. 8$a$.

Figures 9A, 9B:
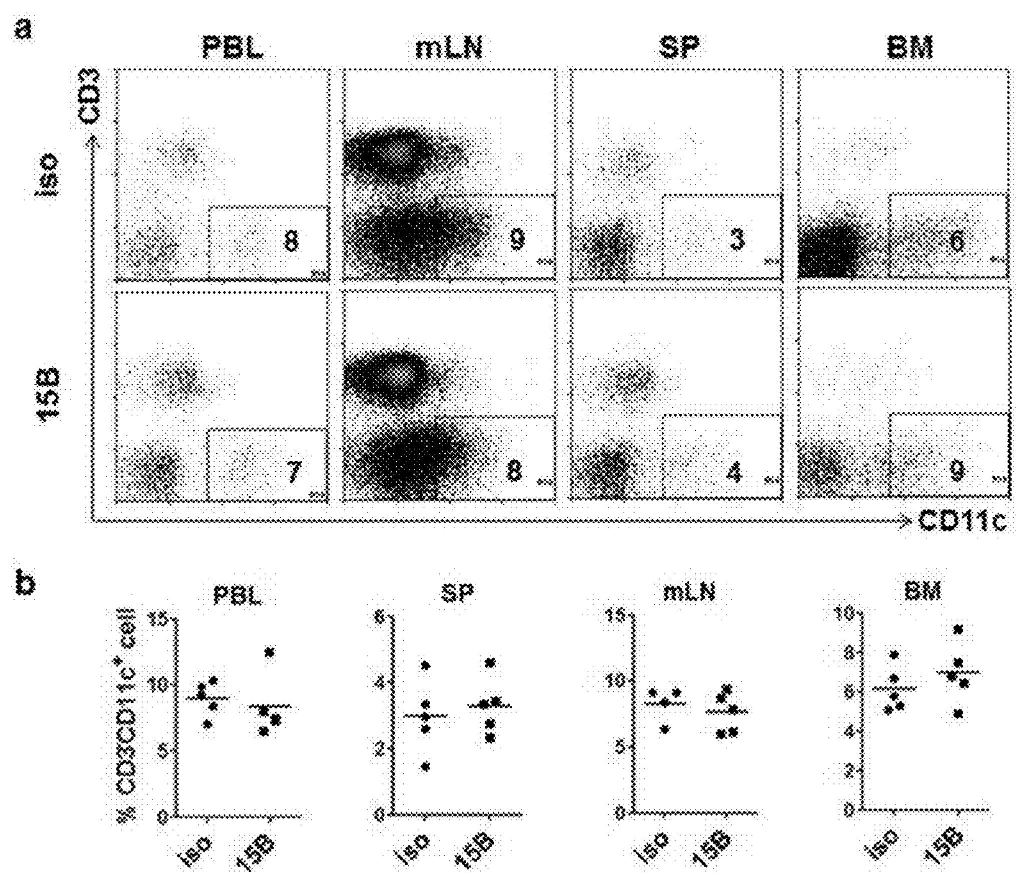

FIGS. 9$a$-9$b$ show specific depletion of pDCs induced by 15B in different lymphoid organs in DKO-hu mice. (a) Representative FACS plots show percentages of CD3-CD14+ cell in huCD45+ cells. (b) Summarized data for FIG. 9$a$. All bars in dot graphs indicate median value.

FIGS. 10$a$-10$d$ show depletion of pDC abolishes IFN-I induction during acute HIV-1 infection in DKO-hu mice. Humanized mice were treated with either 15B or isotype control (iso) antibody. After pDC depletion, humanized mice were infected with HIV-R3A and terminated 8 days post infection (dpi) for analysis. (a) Summarized data of pDC (CD4+CD123+) percentage in total human leukocytes (CD45+) analyzed by FACS. Mock, n=6; isotype+R3A, n=9; 15B+R3A, n=12. (b) Plasma IFNα2 of Mock, HIV-1 infected and 15B treated mice were quantified by Luminex assay. Mock, n=3; isotype+R3A, n=5; 15B+R3A, n=5. (c-d) The mRNA levels of IFN-I and interferon stimulated genes in purified human cells (CD45+) from mouse spleen were measured by real-time PCR. Mock, n=3; isotype+R3A, n=5; 15B+R3A, n=5. All bars in dot graphs indicate median value. Error bars indicate standard deviations (SD). * and ** indicate p<0.05 and p<0.01, respectively.

FIGS. 11$a$-11$e$ show pre-depletion of pDC enhances HIV-1 replication. Humanized mice were infected with HIV-1 three days after pDC depletion and terminated at 8 dpi (R3A, a-b) or three weeks post infection (JR-CSF, c-e). (a) Plasma HIV-1 RNA levels (genome copy#×log 10/ml) were analyzed by real-time PCR. isotype+R3A, n=9; 15B+R3A, n=12. (b) Immunohistochemistry staining for p24 positive cells in spleens. (c) Plasma JR-CSF HIV-1 RNA levels (genome copy#×log 10/ml) were analyzed by real-time PCR at 3 weeks post infection. isotype+JR-CSF, n=12; 15B+JR-CSF, n=12. (d) Representative FACS plots for p24 positive CD4 T cells in spleens at 3 weeks post-infection. (e) Summarized data of relative p24+ T cells. isotype+JR-CSF, n=7; 15B+JR-CSF, n=7. Bars in dot graphs indicate median value. * indicates p<0.05.

FIGS. 12$a$-12$d$ show elevated CD38+DR+CD8 T cells in pDC-depleted mice with elevated HIV-1 infection. (a) Representative FACS plots show CD38 and HLA-DR expression on CD8 T cells induced by R3A infection in peripheral blood and spleen at 8 dpi. (b) Summarized data for FIG. 4$a$. (c) Representative FACS plots show CD8 T cell activation induced by JR-CSF infection at 3 weeks post-infection. (d) Summarized data for FIG. 4$c$. mock, n=6; isotype+R3A, n=9; 15B+R3A, n=12. All bars in dot graphs indicate median value. * and ** indicate p<0.05 and p<0.01, respectively.

Figures 13A, 13B:
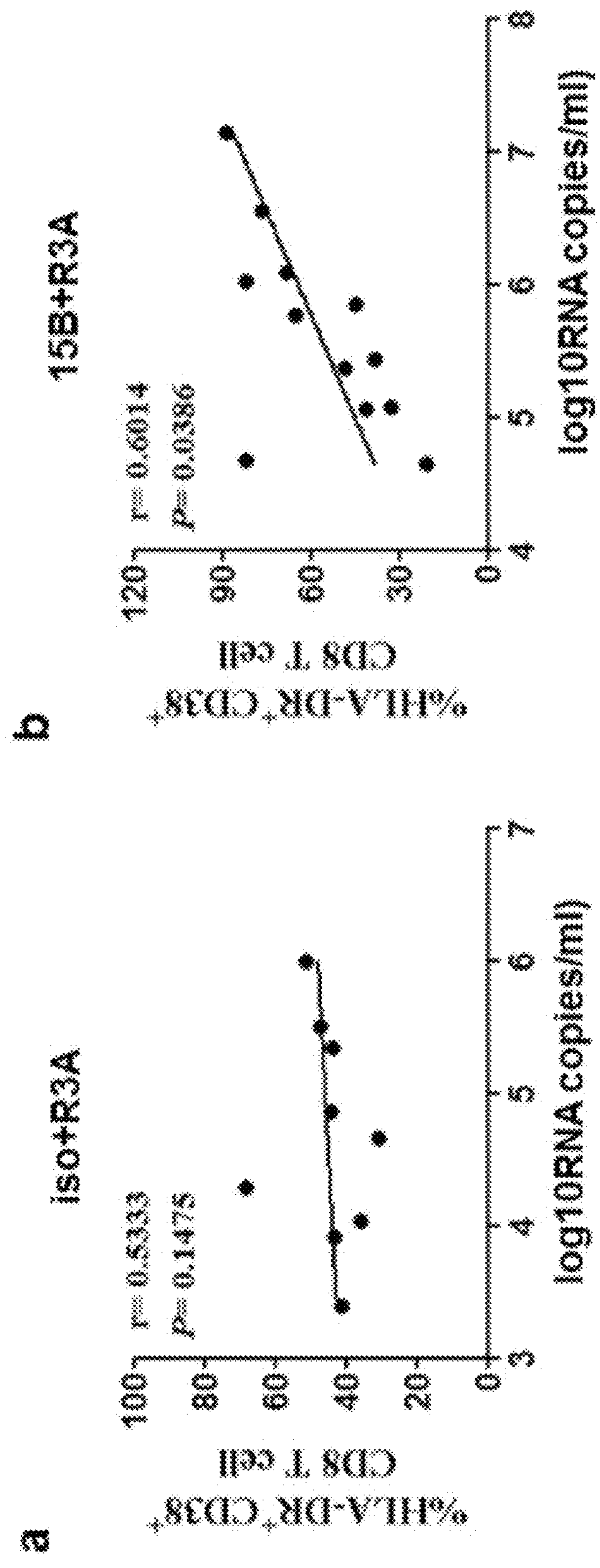

FIGS. 13$a$-13$b$ shows the correlation between CD8 T cell activation in spleen and viral load. Correlations were analyzed with the Spearman nonparametric test. Isotype+R3A, n=9; 15B+R3A, n=12. Squared correlation coefficients (r) and P values are shown.

FIGS. 14$a$-14$e$ show pre-depletion of pDC reduces HIV-1 immunopathogenesis. Humanized mice were infected with HIV-R3A three days after pDC depletion and terminated at 8 dpi. (a-c) Cell counts of human T cells or total leukocytes in peripheral blood and spleen. (a) CD4 T cell (CD34CD8−) counts. (b) CD8 T cell (CD3+CD4-CD8+) counts. (c) Total human CD45+ leukocyte counts. (d-e) Representative histograms and summarized data show percentages of dead CD4 T cells, CD8 T cells and human $CD45^{+}$ cells in spleens. Mock, n=6; isotype+R3A, n=9; 15B+R3A, n=12. All bars in dot graphs indicate median value. * and ** indicate p<0.05 and p<0.01, respectively.

Figures 15A, 15B, 15C:
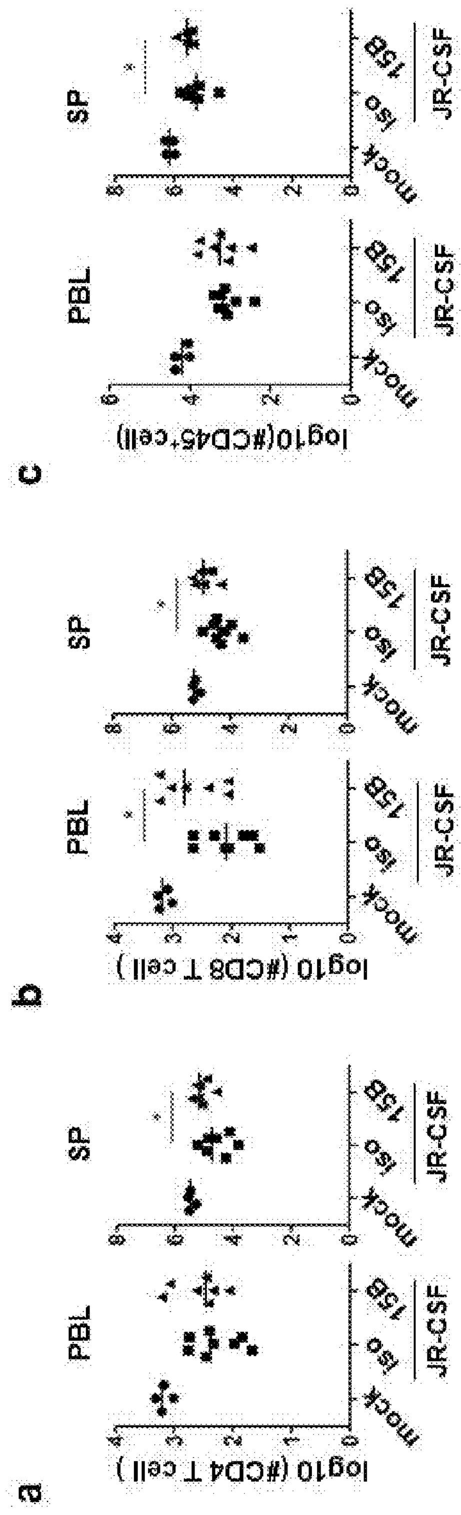

FIGS. 15$a$-15$c$ show pre-depletion of pDC reduced HIV-1 pathogenesis. Humanized mice were infected with HIV-1 three days after pDC depletion and terminated at 3 weeks post-infection. (a-c) Cell counts of human T cells or total leukocytes in peripheral blood and spleen. (a) CD4 T cell (CD3+CD8−) counts. (b) CD8 T cell (CD3+CD4−CD8+) counts. (c) huCD45+ leukocyte counts. Mock, n=4; isotype+JR-CSF, n=8; 15B+JR-CSF, n=7. All bars in dot graphs indicate median value. * indicates p<0.05.

FIGS. 16$a$-16$g$ show depletion of pDC increases HIV-1 replication but reduces HIV-1 immunopathogenesis during chronic HIV-1 infection. HIV-1 infected humanized mice were treated with 15B at 11 weeks post-infection and terminated at 21 weeks post-infection (mock, n=6; JR-CSF+PBS, n=10; JR-CSF+15B, n=9). (a) Plasma HIV-1 RNA levels (genome copy#×log 10/ml) at each time point were analyzed by real-time PCR. (b) Summarized data show percentages of HIV p24 positive CD4 T cells (CD3+CD8−) in spleens. (c-e) Cell counts of human T cells or total CD45 leukocytes in peripheral blood and spleens. (c) CD4 T cell (CD3+CD8−) counts. (d) CD8 T cell (CD3+CD4−CD8+) counts. (e) Human CD45+ leukocyte counts. (f) Immunohistochemistry staining for human CD45+ cells in spleens. (g) Summarized data show percentages of dead CD4 T cells, CD8 T cells and human $CD45^+$ cells in spleens (JR-CSF infection at termination, 21 wpi). Bars in dot graphs indicate median value. * and ** indicate $p<0.05$ and $p<0.01$, respectively.

FIGS. 17*a*-17*f* show depletion of pDC increases HIV-1 replication but reduces type I IFN response in chronic infection. HIV-1 infected humanized mice were started treatment with 15B at 11 weeks post-infection and terminated at 21 weeks post-infection. (a) Representative FACS histograms for FIG. 6*b*. (b) The production of IFN-a2 in plasma from mock (n=4), JR-CSF+PBS (n=5) and JR-CSF+15B (n=5) at either 11 weeks post-infection (pre) or 21 weeks post infection (post), measured by Luminex. (c-d) The mRNA levels of IFN-1 and interferon stimulated genes in purified human cells (CD45+) from mouse spleen were measured by real-time PCR (n=5). (e-f) Relative ISGs gene expression in purified human CD45+ cells (e) and CD8 T cells (CD3+CD4−CD8+) (f) from spleens at termination. All bars in dot graphs indicate median value. Error bars indicate standard deviations (SD). * and ** indicate $p<0.05$ and $p<0.01$, respectively.

FIG. 18 shows the nucleotide sequence (SEQ ID NO:1) and the amino acid sequence (SEQ ID NO:2) of the heavy chain of 15B.

FIG. 19 shows the nucleotide sequence (SEQ ID NO:3) and the amino acid sequence (SEQ ID NO:4) of the light chain of 15B.

Figure 20:
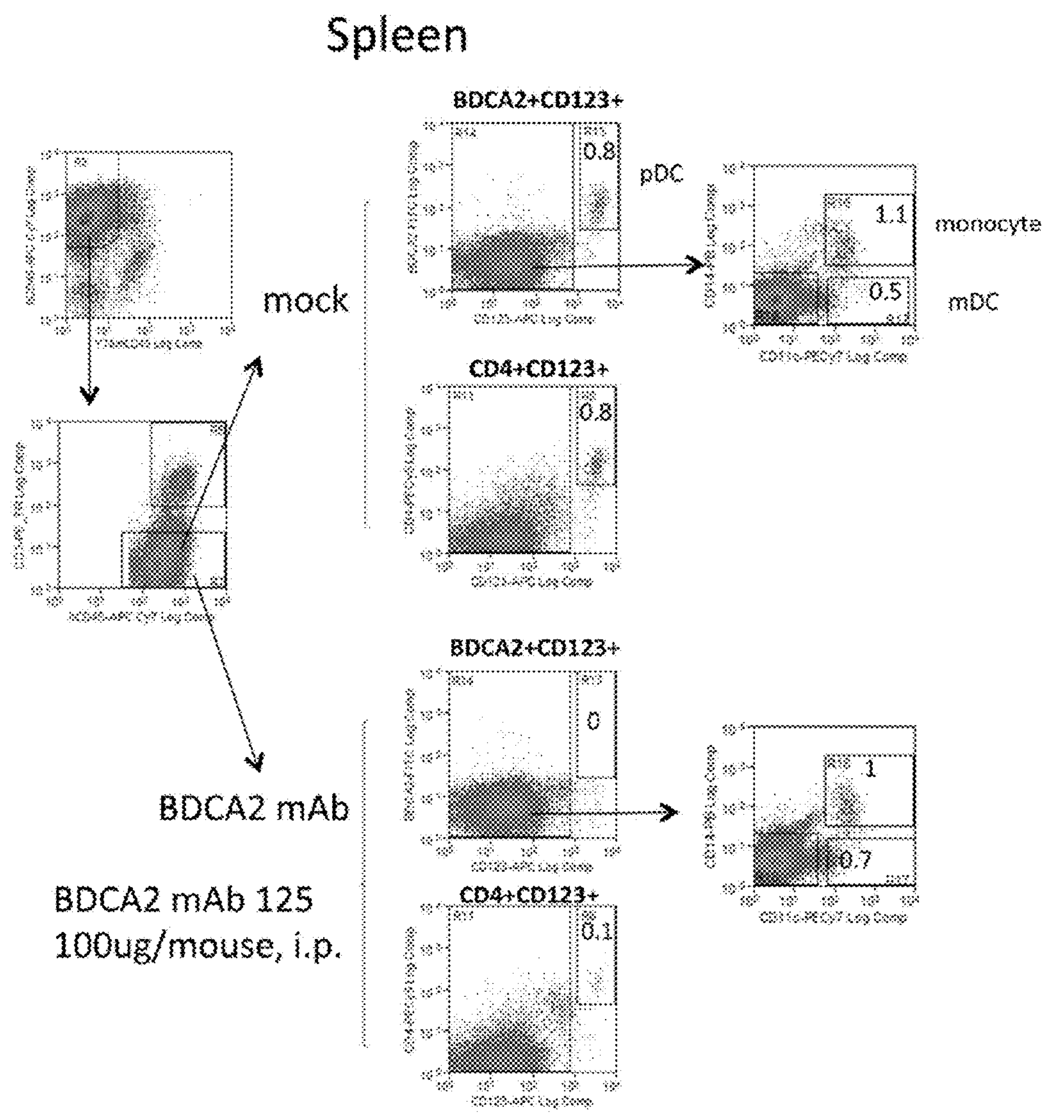
Figure 20:
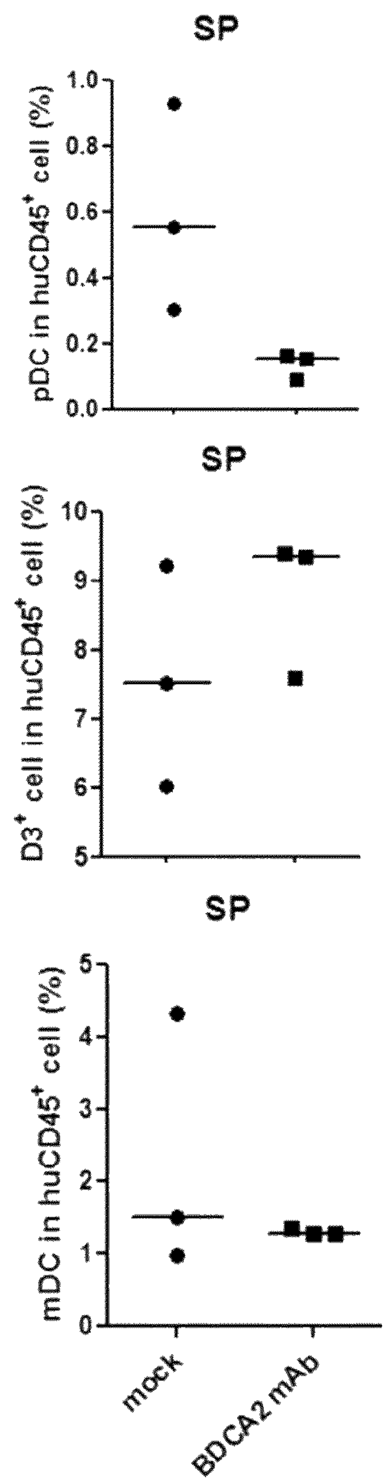

FIG. 20 shows depletion of pDC mediated by 12B (also called 125) in DKO-hu mice.

FIG. 21 shows the nucleotide sequence (SEQ ID NO:5) and the amino acid sequence (SEQ ID NO:6) of the heavy chain of 12B.

FIG. 22 shows the nucleotide sequence (SEQ ID NO:7) and the amino acid sequence (SEQ ID NO:8) of the light chain of 12B.

DETAILED DESCRIPTION OF THE INVENTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

All publications, patent applications, patents, patent publications and other references cited herein are incorporated by reference in their entireties for the teachings relevant to the sentence and/or paragraph in which the reference is presented.

I. Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 USPQ 461, 463 (CCPA 1976) (emphasis in the original); see also MPEP §2111.03.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total often or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in epitope binding activity of at least about 50% or more as compared to the activity of a polypeptide consisting of the recited sequence.

An "effective" amount as used herein is an amount that provides a desired effect.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of HIV infection, reduction in viral load or increase in immune cells). Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

The term "deplete," as used herein with respect to pDC, refers to a measurable decrease in the number of pDC in a subject or in a sample. The reduction can be at least about 10%, e.g., at least about 20%, 30%, 40%, 50%, 60%, 70%, 80%, 90%, 95%, 96%, 97%, 98%, 99%, or more. In certain embodiments, the term refers to a decrease in the number of pDC in a subject or in a sample to an amount below detectable limits.

The phrase "disorder associated with pDC," as used herein, refers to any disease, disorder, or condition in which pDC play a role in a cause, side effect, symptom, or other aspect in the disease, disorder, or condition. Examples of such disorders include, without limitation, infectious diseases, autoimmune disorders, and cancer.

The term "infectious diseases," as used herein, refers to any disease associated with infection by an infectious agent. Examples of infectious agents include, without limitation, viruses and microorganisms. Viruses include, without limitation, Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV) and human T lymphotropic viruses (HITLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B-19; Arenaviridae including Lassa virus; Orthomyxoviridae including influenza viruses; Poxviridae including Orf virus, molluscum contageosum virus, smallpox virus and Monkey pox virus; Togaviridae including Venezuelan equine encephalitis virus; Coronaviridae including corona viruses such as the severe acute respiratory syndrome (SARS) virus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus, TGE virus (swine), Foot and mouth disease virus, simian virus 5, human parainfluenza virus type 2, human metapneuomovirus, enteroviruses, and any other pathogenic virus now known or later identified (see, e.g., *Fundamental Virology*, Fields et al., Eds., 3$^{rd}$ ed., Lippincott-Raven, New York, 1996, the entire contents of which are incorporated by reference herein for the teachings of pathogenic viruses).

Pathogenic microorganisms include, but are not limited to, *Rickettsia, Chlamydia, Mycobacteria, Clostridia, Corynebacteria, Mycoplasma, Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4$^{th}$ ed., Lippincott, New York, 1990, the entire contents of which are incorporated herein by reference for the teachings of pathogenic microorganisms). Specific examples of microorganisms include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum. Bacillus anthracis, Salmonella typhi, Vibrio cholera. Pasteurella pestis* (*Yersinia pestis*), *Pseudomonas aeruginosa, Campylobacter jejuni, Clostridium dificile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli.*

The term "autoimmune disorders," as used herein, refers to any disorder associated with an autoimmune reaction. Examples include, without limitation, multiple sclerosis, Crohn's disease, ulcerative colitis, lupus, inflammatory bowel syndrome, and irritable bowel syndrome.

The term "cancer," as used herein, refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., target protein binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding can be measured using assays that are well known in the art and as described herein.

II. Antibodies and Compositions

The inventors have identified and characterized antibodies that specifically bind to BDCA2 and deplete pDC. Such antibodies can advantageously be used to deplete pDC in a subject, e.g., for research or therapeutic purposes. Such antibodies can be used to treat disorders associated with pDC. Accordingly, one aspect of the invention relates to antibodies or fragments thereof that specifically bind to BDCA2 and depletes pDC when administered to a subject.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. Nos. 4,474,893 or 4,816,567. The antibodies can also be chemically constructed according to the method disclosed in U.S. Pat. No. 4,676,980.

Antibody fragments included within the scope of the present invention include, for example, Fab, Fab', $F(ab')_2$, and Fv fragments; domain antibodies, diabodies; vaccibodies, linear antibodies; single-chain antibody molecules; and multispecific antibodies formed from antibody fragments. Such fragments can be produced by known techniques. For example, $F(ab')_2$ fragments can be produced by pepsin digestion of the antibody molecule, and Fab fragments can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); *Riechmann et al., Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures. The polynucleotide sequence and polypeptide sequence of BDCA2 is known in the art and can be found in sequence databases such as GenBank. Examples of sequences include the human BDCA2 polypeptide sequence (Accession No. Q8WTT0) and polynucleotide sequence (Accession No. AF293615), incorporated herein by reference in their entirety.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for BDCA2. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-bascd immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}$S, $^{125}$S, $^{131}$I), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In one embodiment, the antibody is an antibody or a fragment thereof (e.g., a monoclonal antibody) that specifically binds to BDCA2. The antibody may bind to a specific epitope on BDCA2.

In one embodiment, the antibody is a monoclonal antibody produced by hybridoma cell line 15B. In a further embodiment, the antibody is a monoclonal antibody or a fragment thereof that competes for binding to the same epitope specifically bound by the monoclonal antibody produced by hybridoma cell line 15B. In another embodiment, the antibody is a monoclonal antibody or a fragment thereof that specifically binds to the same epitope specifically bound by the monoclonal antibody produced by hybridoma cell line 15B. The epitope bound by the antibody produced by hybridoma cell line 15B comprises, consists essentially of, or consists of the amino acid sequence IQN-LKRNSSYFLGLSDPGGR (SEQ ID NO:9) or a fragment thereof of at least 5 contiguous amino acids, e.g., at least 5, 6, 7, 8, 9, 10, 11, 12, 13, 14, or 15 or more contiguous amino acids.

In certain embodiments, the monoclonal antibody or a fragment thereof is a chimeric antibody or a humanized antibody. In additional embodiments, the chimeric or humanized antibody comprises at least a portion of the CDRs of the monoclonal antibody produced by hybridoma cell line 15B. As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof, in any combination.

In one embodiment, the antibody or a fragment thereof comprises a heavy chain variable region comprising the amino acid sequence of SEQ ID NO:2 or a sequence at least 90% identical thereto, e.g., at least 95, 96, 97, 98, or 99% identical thereto. In another embodiment, the antibody or a fragment thereof comprises a heavy chain variable region comprising an amino acid sequence encoded by the nucleotide sequence of SEQ ID NO:1 or a sequence at least 90% identical thereto, e.g., at least 95, 96, 97, 98, or 99% identical thereto. In some embodiments, the antibody or fragment thereof comprises a heavy chain variable region comprising at least 50 contiguous amino acids of the amino acid sequence of SEQ ID NO:2 or a sequence at least 90% identical thereto, e.g., at least 100, 150, or 200 or more contiguous amino acids.

In one embodiment, the antibody or a fragment thereof comprises a light chain variable region comprising the amino acid sequence of SEQ ID NO:4 or a sequence at least 90% identical thereto, e.g., at least 95, 96, 97, 98, or 99% identical thereto. In another embodiment, the antibody or a fragment thereof comprises a light chain variable region comprising an amino acid sequence encoded by the nucleotide sequence of SEQ ID) NO:3 or a sequence at least 90% identical thereto, e.g., at least 95, 96, 97, 98, or 99% identical thereto. In some embodiments, the antibody or fragment thereof comprises a light chain variable region comprising at least 50 contiguous amino acids of the amino acid sequence of SEQ ID NO:4 or a sequence at least 90% identical thereto, e.g., at least 100, 150, or 200 or more contiguous amino acids.

In one embodiment, the antibody or a fragment thereof comprises a heavy chain variable region comprising the amino acid sequence of SEQ ID NO:2 or a sequence at least 90% identical thereto, e.g., at least 95, 96, 97, 98, or 99% identical thereto, or encoded by the nucleotide sequence of SEQ ID NO: 1 or a sequence at least 90% identical thereto, e.g., at least 95, 96, 97, 98, or 99% identical thereto, and a light chain variable region comprising the amino acid sequence of SEQ ID NO:4 or a sequence at least 90% identical thereto, e.g., at least 95, 96, 97, 98, or 99% identical thereto, or encoded by the nucleotide sequence of SEQ ID NO:3 or a sequence at least 90% identical thereto, e.g., at least 95, 96, 97, 98, or 99% identical thereto. In some embodiments, the antibody or fragment thereof comprises a heavy chain variable region comprising at least 50 contiguous amino acids of the amino acid sequence of SEQ ID NO:2 or a sequence at least 90% identical thereto, e.g., at least 100, 150, or 200 or more contiguous amino acids, and a light chain variable region comprising at least 50 contiguous amino acids of the amino acid sequence of SEQ ID NO:4 or a sequence at least 90% identical thereto, e.g., at least 100, 150, or 200 or more contiguous amino acids.

In one embodiment, the antibody or a fragment thereof comprises a heavy chain variable region comprising at least one CDR (e.g., 1, 2, or 3) or a portion thereof from the amino acid sequence of SEQ ID NO:2 or a sequence at least 90% identical thereto, e.g., at least 95, 96, 97, 98, or 99% identical thereto. In another embodiment, the antibody or a fragment thereof comprises a heavy chain variable region comprising at least one CDR (e.g., 1, 2, or 3) or a portion thereof from an amino acid sequence encoded by the nucleotide sequence of SEQ ID NO:1 or a sequence at least 90% identical thereto, e.g., at least 95, 96, 97, 98, or 99% identical thereto. One of skill in the art understands that the CDRs play an important role in binding specificity and that sequence substitutions (e.g., for humanization of a mouse antibody) are preferably made outside of the CDRs and that minimal changes are made within the CDRs. Thus, in some embodiments, sequences that are at least 90% identical to the disclosed sequences comprise no changes or only a minimal number of changes to the CDRs.

In one embodiment, the antibody or a fragment thereof comprises a light chain variable region comprising at least one CDR (e.g., 1, 2, or 3) or a portion thereof from the amino acid sequence of SEQ ID NO:4 or a sequence at least 90% identical thereto, e.g., at least 95, 96, 97, 98, or 99% identical thereto. In another embodiment, the antibody or a fragment thereof comprises a light chain variable region comprising at least one CDR (e.g., 1, 2, or 3) or a portion thereof from an amino acid sequence encoded by the nucleotide sequence of SEQ ID NO:3 or a sequence at least 90% identical thereto, e.g., at least 95, 96, 97, 98, or 99% identical thereto.

In one embodiment, the antibody or a fragment thereof comprises a heavy chain variable region comprising at least one CDR (e.g., 1, 2, or 3) from the amino acid sequence of SEQ ID NO:2 or a sequence at least 90% identical thereto, e.g., at least 95, 96, 97, 98, or 99% identical thereto, or encoded by the nucleotide sequence of SEQ ID NO: 1 or a sequence at least 90% identical thereto, e.g., at least 95, 96, 97, 98, or 99% identical thereto, and a light chain variable region comprising at least one CDR (e.g., 1, 2, or 3) from the amino acid sequence of SEQ ID NO:4 or a sequence at least 90% identical thereto, e.g., at least 95, 96, 97, 98, or 99% identical thereto, or encoded by the nucleotide sequence of SEQ ID NO:3 or a sequence at least 90% identical thereto, e.g., at least 95, 96, 97, 98, or 99% identical thereto.

In one embodiment, the antibody is a monoclonal antibody produced by hybridoma cell line 12B (previously called 125). In a further embodiment, the antibody is a monoclonal antibody or a fragment thereof that competes for binding to the same epitope specifically bound by the monoclonal antibody produced by hybridoma cell line 12B. In another embodiment, the antibody is a monoclonal antibody or a fragment thereof that specifically binds to the same epitope specifically bound by the monoclonal antibody produced by hybridoma cell line 12B. In certain embodiments, the monoclonal antibody or a fragment thereof is a chimeric antibody or a humanized antibody. In additional embodiments, the chimeric or humanized antibody comprises at least a portion of the CDRs of the monoclonal antibody produced by hybridoma cell line 12B.

In one embodiment, the antibody or a fragment thereof comprises a heavy chain variable region comprising the amino acid sequence of SEQ ID NO:6 or a sequence at least 90% identical thereto, e.g., at least 95, 96, 97, 98, or 99% identical thereto. In another embodiment, the antibody or a fragment thereof comprises a heavy chain variable region comprising an amino acid sequence encoded by the nucleotide sequence of SEQ ID NO:5 or a sequence at least 90% identical thereto, e.g., at least 95, 96, 97, 98, or 99% identical thereto. In some embodiments, the antibody or fragment thereof comprises a heavy chain variable region comprising at least 50 contiguous amino acids of the amino acid sequence of SEQ ID NO:6 or a sequence at least 90% identical thereto, e.g., at least 100, 150, or 200 or more contiguous amino acids.

In one embodiment, the antibody or a fragment thereof comprises a light chain variable region comprising the amino acid sequence of SEQ ID NO:8 or a sequence at least 90% identical thereto, e.g., at least 95, 96, 97, 98, or 99% identical thereto. In another embodiment, the antibody or a fragment thereof comprises a light chain variable region comprising an amino acid sequence encoded by the nucleotide sequence of SEQ ID NO:7 or a sequence at least 90% identical thereto, e.g., at least 95, 96, 97, 98, or 99% identical thereto. In some embodiments, the antibody or fragment thereof comprises a light chain variable region comprising at least 50 contiguous amino acids of the amino acid sequence of SEQ ID NO:8 or a sequence at least 90% identical thereto, e.g., at least 100, 150, or 200 or more contiguous amino acids.

In one embodiment, the antibody or a fragment thereof comprises a heavy chain variable region comprising the amino acid sequence of SEQ ID NO:6 or a sequence at least 90% identical thereto, e.g., at least 95, 96, 97, 98, or 99% identical thereto, or encoded by the nucleotide sequence of SEQ ID NO:5 or a sequence at least 90% identical thereto, e.g., at least 95, 96, 97, 98, or 99% identical thereto, and a light chain variable region comprising the amino acid sequence of SEQ ID NO:8 or a sequence at least 90% identical thereto, e.g., at least 95, 96, 97, 98, or 99% identical thereto, or encoded by the nucleotide sequence of SEQ ID NO:7 or a sequence at least 90% identical thereto, e.g., at least 95, 96, 97, 98, or 99% identical thereto. In some embodiments, the antibody or fragment thereof comprises a heavy chain variable region comprising at least 50 contiguous amino acids of the amino acid sequence of SEQ ID NO:6 or a sequence at least 90% identical thereto, e.g., at least 100, 150, or 200 or more contiguous amino acids, and a light chain variable region comprising at least 50 contiguous amino acids of the amino acid sequence of SEQ ID NO:8 or a sequence at least 90% identical thereto, e.g., at least 100, 150, or 200 or more contiguous amino acids.

In one embodiment, the antibody or a fragment thereof comprises a heavy chain variable region comprising at least one CDR (e.g., 1, 2, or 3) or a portion thereof from the amino acid sequence of SEQ ID NO:6 or a sequence at least 90% identical thereto, e.g., at least 95, 96, 97, 98, or 99% identical thereto. In another embodiment, the antibody or a fragment thereof comprises a heavy chain variable region comprising at least one CDR (e.g., 1, 2, or 3) or a portion thereof from an amino acid sequence encoded by the nucleotide sequence of SEQ ID NO:5 or a sequence at least 90% identical thereto, e.g., at least 95, 96, 97, 98, or 99% identical thereto. One of skill in the art understands that the CDRs play an important role in binding specificity and that sequence substitutions (e.g., for humanization of a mouse antibody) are preferably made outside of the CDRs and that minimal changes are made within the CDRs. Thus, in some embodiments, sequences that are at least 90% identical to the disclosed sequences comprise no changes or only a minimal number of changes to the CDRs.

In one embodiment, the antibody or a fragment thereof comprises a light chain variable region comprising at least one CDR (e.g., 1, 2, or 3) or a portion thereof from the amino acid sequence of SEQ ID NO:8 or a sequence at least 90% identical thereto, e.g., at least 95, 96, 97, 98, or 99% identical thereto. In another embodiment, the antibody or a fragment thereof comprises a light chain variable region comprising at least one CDR (e.g., 1, 2, or 3) or a portion thereof from an amino acid sequence encoded by the nucleotide sequence of SEQ ID NO:7 or a sequence at least 90% identical thereto, e.g., at least 95, 96, 97, 98, or 99% identical thereto.

In one embodiment, the antibody or a fragment thereof comprises a heavy chain variable region comprising at least one CDR (e.g., 1, 2, or 3) from the amino acid sequence of SEQ ID NO:6 or a sequence at least 90% identical thereto, e.g., at least 95, 96, 97, 98, or 99% identical thereto, or encoded by the nucleotide sequence of SEQ ID NO:5 or a sequence at least 90% identical thereto, e.g., at least 95, 96, 97, 98, or 99% identical thereto, and a light chain variable region comprising at least one CDR (e.g., 1, 2, or 3) from the amino acid sequence of SEQ ID NO:8 or a sequence at least 90% identical thereto, e.g., at least 95, 96, 97, 98, or 99% identical thereto, or encoded by the nucleotide sequence of SEQ ID NO:7 or a sequence at least 90% identical thereto, e.g., at least 95, 96, 97, 98, or 99% identical thereto.

As a further aspect, the invention provides compositions comprising the antibodies or fragments thereof of the invention. In some embodiments, the compositions are pharmaceutical formulations comprising the antibodies of the invention in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis/tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer, Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

A further aspect of the invention relates to kits for use in the methods of the invention. The kit can comprise the antibody of the invention in a form suitable for administration to a subject or in a form suitable for compounding into a formulation. The kit can further comprise other components, such as therapeutic agents, carriers, buffers, containers, devices for administration, and the like. The kit can be designed for therapeutic use, diagnostic use, and/or research use and the additional components can be those suitable for the intended use. The kit can further comprise labels and/or instructions, e.g., for treatment of a disorder, Such labeling and/or instructions can include, for example, information concerning the amount, frequency and method of administration of the antibody.

III. Methods

As one aspect, the invention provides methods of depleting pDC in a subject, comprising delivering to the subject an effective amount of an antibody or a fragment thereof that specifically binds to BDCA2 and depletes pDC, thereby depleting pDC. In some embodiments, pDC are depleted by at least about 50% relative to subjects that have not received the antibody or fragment thereof, e.g., at least 60%, 70%, 80%, 90%, 95%, 96%, 97%, 98%, or 99% or more. In other embodiments, the invention provides methods of reducing the number of and/or depleting pDC in a sample ex vivo or in vitro, e.g., a mixed population of cells, comprising delivering to the sample an effective amount of an antibody or a fragment thereof that specifically binds to BDCA2 and reduces the number of and/or depletes pDC, thereby reducing the number of and/or depleting pDC.

In a further aspect, the invention provides methods of treating a disorder associated with pDC in a subject, comprising delivering to the subject a therapeutically effective an antibody or a fragment thereof that specifically binds to BDCA2 and reduces the number of and/or depletes pDC, thereby treating the disorder.

In some embodiments, the subject is a research subject, e.g., a laboratory animal. In other embodiments, the subject is one that has been diagnosed with a disorder associated with pDC. In another embodiment, the subject may be one that is at risk of developing a disorder associated with pDC (e.g., predisposed due to hereditary factors, exposure to a pathogen, abnormal immune cell counts, etc.). Disorders associated with pDC include, without limitation, infectious diseases or persistent virus infection (e.g., HIV infection), autoimmune disease (e.g., systemic lupus erythematosus), and cancer (e.g., pDC-derived leukemia), and disorders associated with tissue accumulation of pDC.

The antibodies of the present invention can optionally be delivered in conjunction with other therapeutic agents. The additional therapeutic agents can be delivered concurrently with the antibodies of the invention. As used herein, the word "concurrently" means sufficiently close in time to produce a combined effect (that is, concurrently can be simultaneously, or it can be two or more events occurring within a short time period before or after each other).

In one embodiment, the antibodies of the invention are administered in conjunction with anti-cancer agents, such as 1) *vinca* alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In another embodiment, the compounds of the invention are administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib.

In one embodiment, the antibodies of the invention are administered in conjunction with antiviral agents including, for example, virus-inactivating agents such as nonionic, anionic and cationic surfactants, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants, e.g., sorbitan monolaurate, may advantageously be used as antiviral agents in the compositions described herein. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. From these reverse transcriptase inhibitors, agents and their analogs that have shown poor oral bioavailability are especially suitable for administration to mucosal tissue, in combination with antibodies and compositions of the invention, to prevent sexual transmission of HIV. Other antiviral agents that may be used are those in the category of HIV entry blockers, such as cyanovirin-N, cyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

In one embodiment, the antibodies of the invention are administered in conjunction with immunosuppressive agents including, for example, cyclosporine A, rapamycin, glucocorticoids, azathioprine, mizoribine, aspirin derivatives, hydroxychloroquine, methotrexate, cyclophosphamide and FK506 (tacrolimus).

In particular embodiments, the antibody is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of the antibody will vary somewhat patient to patient, and will depend upon the condition of the patient and the route of delivery. As a general proposition, a dosage from about 0.1 to about 50 mg/kg will have therapeutic efficacy. Toxicity concerns at the higher level can restrict intravenous dosages to a lower level such as up to about 10 mg/kg. A dosage from about 10 mg/kg to about 50 mg/kg can be employed for oral administration. Typically, a dosage from about 0.5 mg/kg to 5 mg/kg can be employed for intramuscular injection.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications as well as research applications. As used herein, the term "subject" refers to humans and other animals. Suitable subjects include mammals such as humans, as well as those mammals of importance due to being endangered, such as Siberian tigers; of economic importance, such as animals raised on farms; animals of social importance to humans, such as animals kept as pets or in zoos; and research animals, such as mice, rabbits, guinea pigs, ferrets, dogs, cats, monkeys, and apes. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; horses; and poultry.

The present invention is more particularly described in the following examples that are intended as illustrative only since numerous modifications and variations therein will be apparent to those skilled in the art.

EXAMPLE 1

Experimental Methods

Construction of Humanized Mice: Approval for animal work was obtained from the University of North Carolina Institutional Animal Care and Use Committee (IACUC). We constructed Balb/C rag2-gammaC (DKO) mutant DKO-hu HSC or Nod-rag1-gammaC (NRG) NRG-hu HSC mice similarly as previously reported[50]. Briefly, human CD34+ cells were isolated from 16- to 20-week-old fetal liver tissues. Tissues were digested with Liver Digest Medium (Invitrogen, Frederick, Md.). The suspension was filtered through a 70 μm cell strainer (BD Falcon, Lincoln Park, N.J.) and was centrifuged at 150 g for 5 minutes to isolate mononuclear cells by Ficoll. After selection with the CD34+ magnetic-activated cell sorting (MACS) kit, CD34+HSCs ($0.5\times10^6$) were injected into the liver of each 2- to 6-days old DKO or NRG mice, which had been previously irradiated at 300 rad. More than 95% of the humanized mice were stably reconstituted with human leukocytes in the blood (10%-90% at 12-14 weeks). Each cohort (humanized mice reconstituted from the same human donor fetal liver tissue) had similar levels of engraftment. All mice were housed at the University of North Carolina at Chapel Hill.

HIV-1 Virus Stocks and Infection of Humanized Mice: HIV-R3A, generated by cloning a highly pathogenic dual tropic envelope into NL4-3 backbone[24,25,51], was used for acute infection experiment. An R5 tropic strain of HIV-1, JR-CSF, was used for both acute and chronic infection. All viruses were generated by transfection of 293T cells. Humanized mice with stable human leukocyte reconstitution were infected with HIV-R3A or JR-CSF, at a dose of 10 ng p24/mouse, through intravenous injection (i.v.). Humanized mice infected with 293T mock supernatant were used as control groups.

Depletion of Human Plasmacytoid Dendritic Cells (pDC) in Humanized Mice: A monoclonal antibody specific to blood dendritic cell antigen-2 (BDCA2), 15B, was used to treat humanized mice through intraperitoneal injection (i.p., 4 mg/kg). For acute HIV-1 infection, humanized mice were injected three times with 15B on −5, −3 and −1 days before infection. For chronic HIV-1 infection, 15B was applied to mice at 11 weeks post-infection (wpi) by injecting twice every week for 10 weeks.

HIV-1 Viral Load Detection: Viral genomic RNA in plasma was extracted using QIAamp® Viral RNA Mini Kit (QIAGEN, cat #52904) according to the manufacture's instruction. HIV-1 replication (genome copy/ml in the plasma) was measured by Real-Time PCR (ABI Applied Biosystem).

Animal Termination and Tissue Processing: For acute HIV-1 infection, mice were terminated at 1 wpi (NL4-R3A) or 3 wpi (JR-CSF). For chronic JR-CSF infection, mice were terminated at 21 wpi. On termination, total leukocytes were isolated from mouse lymphoid organs as previously described[50,52]. Lymphoid tissues, including peripheral blood (PBL), mesenteric lymph nodes (mLN), spleen (SP) and bone marrow (BM) were harvested for analysis. Red blood cells were lysed with ACK buffer, and the remaining cells were stained and fixed with 1% (wt/vol) formaldehyde before FACS analysis. Total cell number was quantified by Guava Easycytes with Guava Express software (Guava).

Flow Cytometry: For HIV-1 gag p24 staining, cells were stained with surface antibodies first, then permeabilized with cytofix/cytoperm buffer (BD Bioscience, cat #554714), followed by intracellular staining. Human leukocytes (mCD45-huCD45+) were analyzed for human CD3, CD4, CD8, CD123, HLA-DR and CD38 by CyAn FACS machine (Dako). FITC-conjugated anti-human HLA-DR (clone: L243, cat #307604), PE-conjugated anti-human CD38 (clone: HIT2, cat #303506), PE/Cy5-conjugated anti-human CD4 (clone: RP4-T4, cat #300510), PE/Cy7-conjugated anti-human CD3 (clone: HIT3a, cat #300316), Pacific blue-conjugated anti-human CD3 (clone: UCHT1, cat #300431), PE/Cy7-conjugated anti-human CD8 (clone: HIT8a, cat #300914), APC-conjugated human CD123 (clone: 6H6, cat #306012) and APC/Cy7-conjuaged anti-human CD45 (clone: H130, cat #304014) were purchased from Biolegend; PE-conjugated anti-human caspase-3 (clone: C92-605, cat #51-68655X) was purchased from BD Bioscience. Pacific orange-conjugated anti-mouse CD45 (clone: H130, cat#MHCD4530), PE/Texas red-conjugated anti-human CD4 (clone: S3.5, cat#MHCD0417) or CD8 (clone: 3B5, cat#MHCD0817), and LIVEDEAD) Fixable Aqua Dead Cell Stain Kit (cat#L34957) were purchased from Invitrogen. FITC-conjugated anti-HIV p24 (clone: FH190-1-1, cat #6604665) was purchased from Beckman Coulter. The cells were analyzed on a CyAn ADP (Dako).

Human Cytokine Luminex Assay: Cytokines in the mouse plasma were quantified with Milliplex®MAP uman Cytokine/Chemokine Magnetic Bead Panel Immunoassay (Millipore). Plasma samples were collected and stored at −80° C. before analysis. The assays were performed at Clinical Proteomics Laboratory at University of North Carolina at Chapel Hill.

Immunohistochemistry: Paraffin-embedded spleen sections from humanized mice were stained with the mouse anti-human huCD45 antibody (Dako, cat#N1514), washed in PBS, then incubated with Mouse-&-Rabbit-on-Rodent Double Stain Polymer (BIOCARE MEDICAL, cat#RDS513H) and substrate DAB (BIOCARE MEDICAL, cat#BDB2004 H, L, MM). Images were captured using a QImaging Micropublisher 3.3 CCD digital camera and QCapture software version 3.0 (QImaging, Surrey, BC).

Cell purification by FACS sorting: Spleen cells from mock or treated groups of mice were pooled. For human CD45+ cells sorting, total m spleen were stained with human CD45, mouse CD45 and 7-Aminoactinomycin D (7-AAD). For human CD8+ T cell sorting, CD3 and CD8 antibody were added to the antibody mix. Cell sorting was performed by the UNC Flow Cytometry Core.

Agilent Microarray Assay: RNA purification was done using RNeasy® Plus Mini Kit (QIAGEN, cat #74134) according to the manufacture's instruction. DNase-RNase free (QIAGEN) treatment was added to the column to eliminate any potential DNA contamination during RNA preparations. Total RNA was checked for quantity, purity and integrity by capillary electrophoresis. RNA was amplified with Cy3- and Cy5-labeled CTP in separate reactions to produce differentially labeled samples and reference c-DNAs. 200 to 400 ng of total RNA were used as a starting material to prepare cDNA. Both were hybridized to the same microarray (UNC Genomic and Bioinformatics Core) using SurePrint G3 Human Gene Expression 8×60K Microarray Kit (Agilent). Agilent Feature Extraction v18 software was used to analyze all images. Gene expression values were quantified by the log 2 ratio of red channel intensity (mean) vs. green channel intensity (mean), followed by LOWESS normalization to remove the intensity dependent dye bias[53].

Cellular mRNA Level Detection: Interferon alpha-1/13 (IFNα1/13), interferon alpha-2 (IFNα2), interferon beta (IFNβ)[54], interferon gamma (IFNγ)[55] and tumor necrosis factor alpha (TNFα)[56] were detected. Type I interferon stimulated genes, MxA[57] and TRIM22[58], were detected to confirm pDCs depletion effect on type I IFN production. Real-time PCR assay was performed (ABI Applied Biosystem). All samples were tested in triplicate using the human GAPDH gene 59 for data normalization.

Statistical Analysis: Data were analyzed using GraphPad Prism software version 5.0 (GraphPad software, San Diego, Calif., USA). The methods used for analysis of microarray data were described above. The data from different cohorts of mice were compared using a 2-tailed Mann-Whitney U test. For gene expression, mean-ΔCT was calculated as the average (±SD) of all ΔCT values within each group of samples and 2-way ANOVA method was used. Correlations were estimated with a Spearman test. All results were considered significant when $p<0.05$.

EXAMPLE 2

HIV-1 Infection in Humanized Mice

Figures 1A, 1B, 1C, 1D, 1E, 1F:
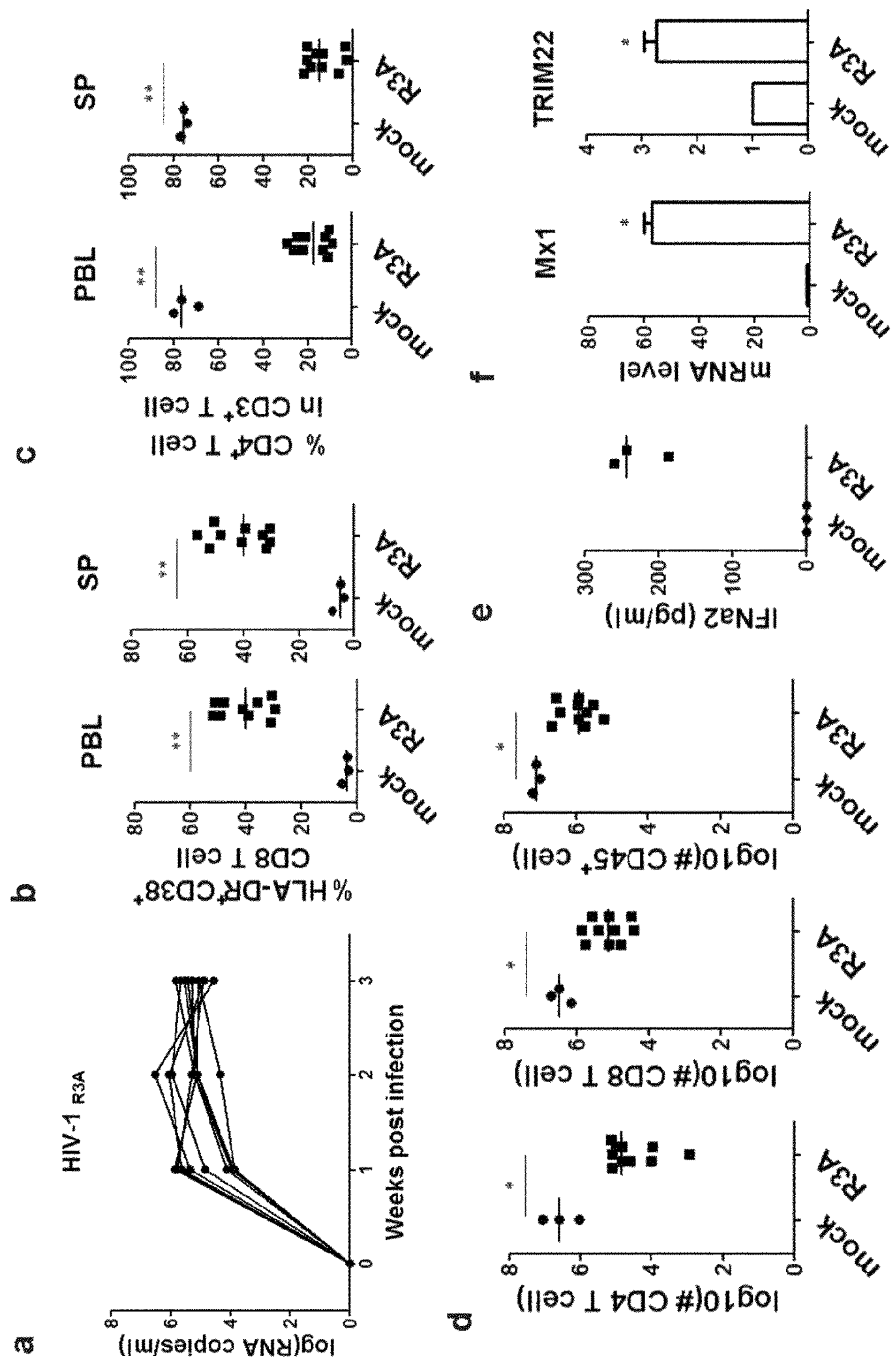
FIGS. 1*a*-1*f* show HIV-1 infection and immune-pathogenesis in humanized mice infected with the pathogenic HIV-R3A isolate. (a) Viral RNA genome copy numbers in plasma from mice inoculated with 1 ng p24/mouse of R3A (n=10). (b) Summary data for the percentages of HLA-DR+ CD38+CD8 T cells (CD3+CD4−CD8+) in peripheral blood and spleen measured by FACS. (c) Summary data for the relative CD4+ T cells (CD3+CD8−CD4+) in total CD3+ T cells. (d) Comparison of absolute CD4 T-cell, CD8 T-cell and huCD45+ cell numbers in spleen from uninfected control mice (n=3) and R3A-infected mice (n=10). (e) The production of IFN-α2 in plasma from uninfected (n=3) and infected (n=3) DKO-hu mice measured by luminex. (f) The relative level of Mx1 and TRIM22 gene expression in huCD45+ cell in spleen (n=3). All bars in dot graphs indicate median value. Error bars indicate standard deviations (SD). * and ** indicate $p<0.05$ and $p<0.01$, respectively.
Figure 2:
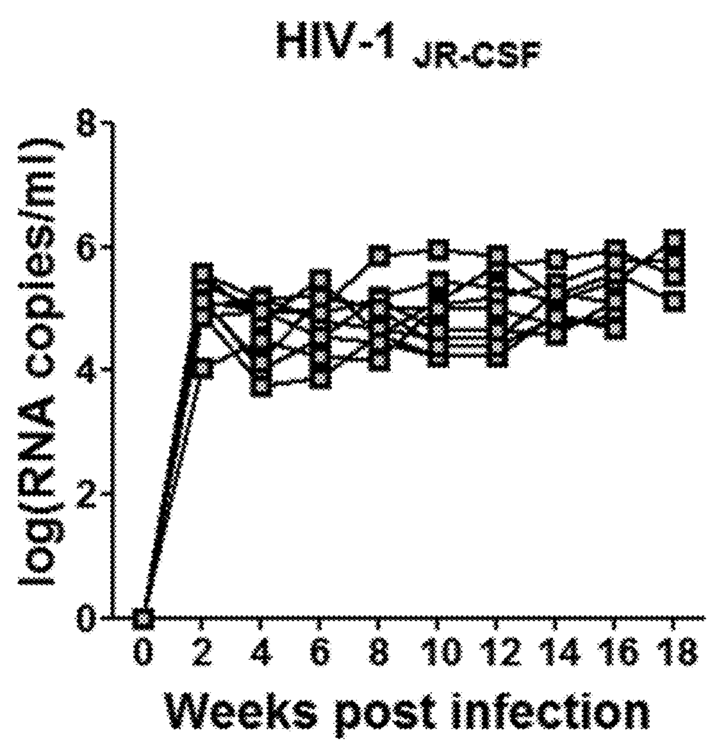
FIG. 2 shows the kinetics of viremia in individual CCR5-tropic JR-CSF-infected DKO-hu mouse measured by quantitative real-time PCR (n=10).
Figures 5A, 5B, 5C:
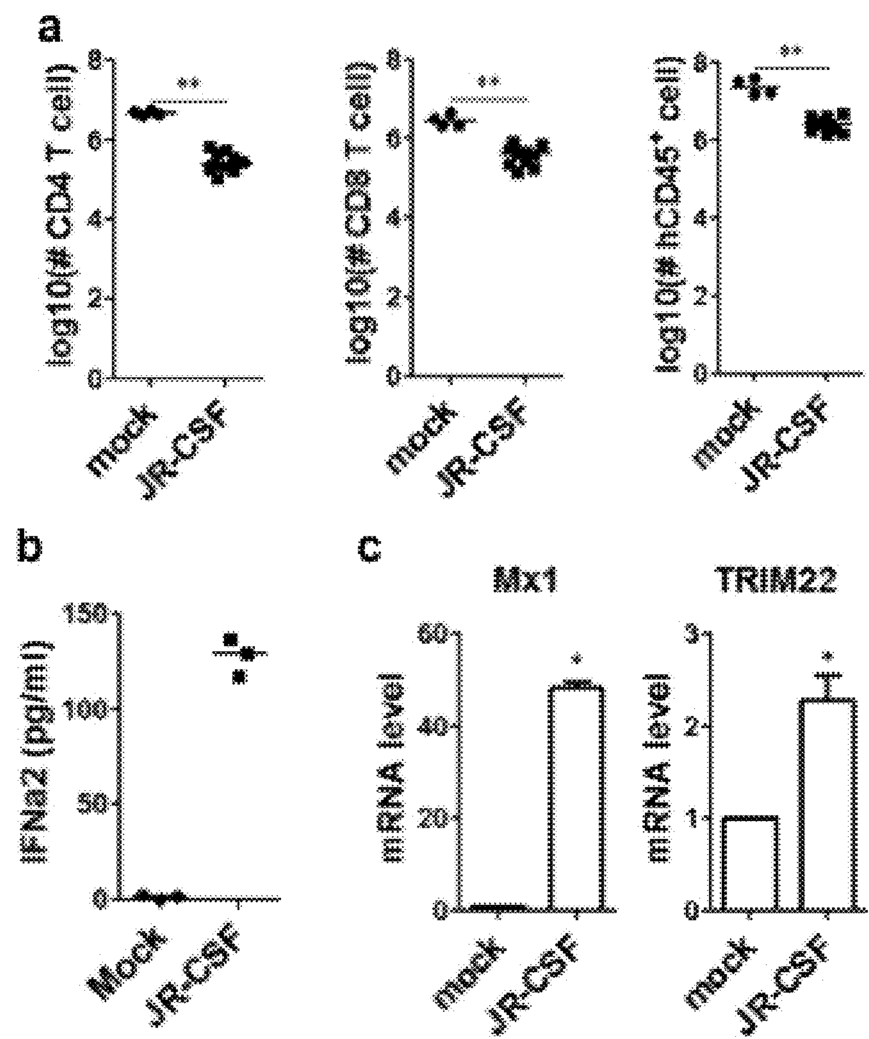

Others and we have reported that functional human pDC are developed in lymphoid tissues in humanized mouse models (Traggiai et al., *Science* 304:104 (2004); Zhang et al., *Blood* 117:6184 (2011); Tanaka et al., *J. Immunol.* (2012)). Human pDC are rapidly activated by HIV-1 infection and the level of pDC activation is reversely correlated with CD4+ T-cell numbers (Zhang et al., *Blood* 117:6184 (2011)), which is consistent with the observation from HIV-1 infected patients (Buimovici-Klein et al., *Lancet* 2:344 (1983); Buimovici-Klein et al., *AIDS Res.* 2:99-108 (1986); Meier et al., *Nature Medicine* 15:955 (2009)) and SIV infected monkeys (Harris et al., *J. Virol.* 84:7886 (2010); Campillo-Gimenez et al., *J. Virol.* 84:1838 (2010)). In this study it was shown that persistent HIV infection is efficiently established in humanized mice infected with either the dual-tropic R3A strain (FIG. 1*a*) or CCR5-tropic JR-CSF strain (FIG. 2). In both acute and chronic HIV-1 infection, an increase of HLA-$DR^+CD38^+$CD8 T cells was observed (FIG. 1*b*, FIGS. 3*a*-3*c*), along with a decrease of CD4 T cell percentage in $CD3^+$ T cell (FIG. 1*c*, FIGS. 4*a*-4*c*). As in HIV-1 patients, leukocytopenia, or depletion of total human $CD45^+$ leukocytes including CD8 T cells, also occurred in the blood and spleen (FIG. 1*d*, FIG. 5*a*). Similar as in HIV patients, there was a significant induction of type I interferon production in plasma in either R3A or JR-CSF infected mice (FIG. 1*e*, FIG. 5*b*), accompanied with an increase of type I interferon specific ISO genes expression in leukocytes from spleen (FIG. 1*f*, FIG. 5*c*). Thus, humanized mice provide a relevant in vivo model for studying the role of HIV-1 and host immune effectors in HIV-1 immunopathogenesis (Zhang et al., *Blood* 117:6184 (2011); Zhang et al., *Cell. Mol. Immunol.* 9:237 (2012)).

EXAMPLE 3

Depletion of Plasmacytoid Dendritic Cells in Humanized Mice

Figures 6A, 6B:
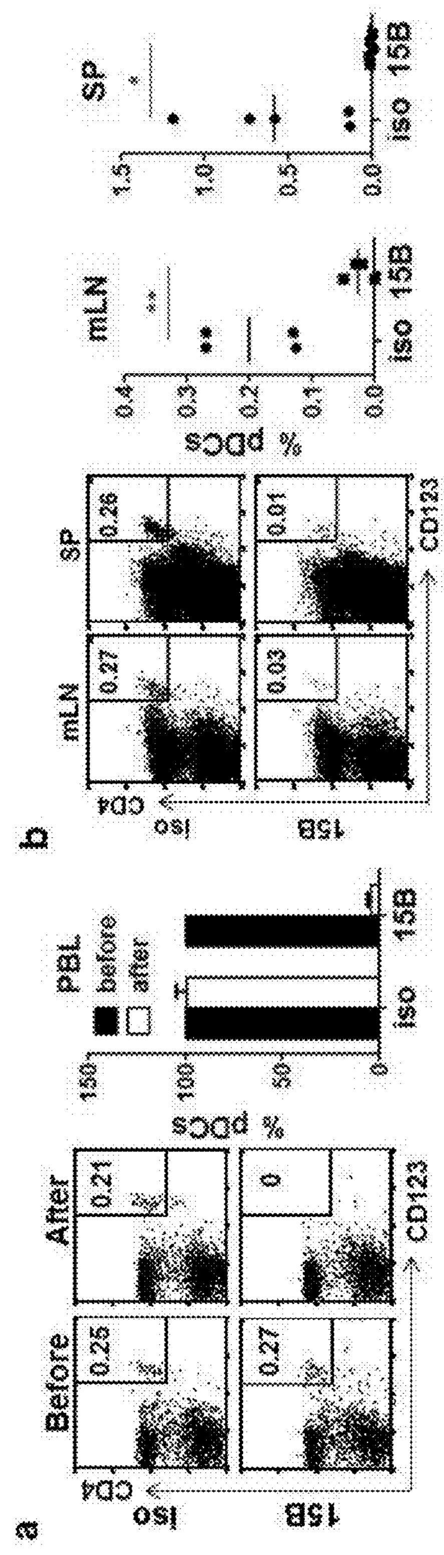

In order to delineate the role of human pDC in HIV-1 infection and pathogenesis in vivo, an anti-BDCA2 (CD303) monoclonal antibody (15B) was developed, which could specifically deplete human pDC in lymphoid organs of humanized mice. After 15B injection, human pDC in $CD45^+$ leukocytes was greatly reduced in both peripheral blood (FIG. 6*a*) and lymphoid organs (FIG. 6*b*). As controls, human T, B, monocytes/macrophages and myeloid dendritic cells were not perturbed by 15B injection (FIGS. 7-9).

EXAMPLE 4

Role of Plasmacytoid Dendritic Cells in Acute HIV-1 Infection

Figures 10A, 10B, 10C, 10D:
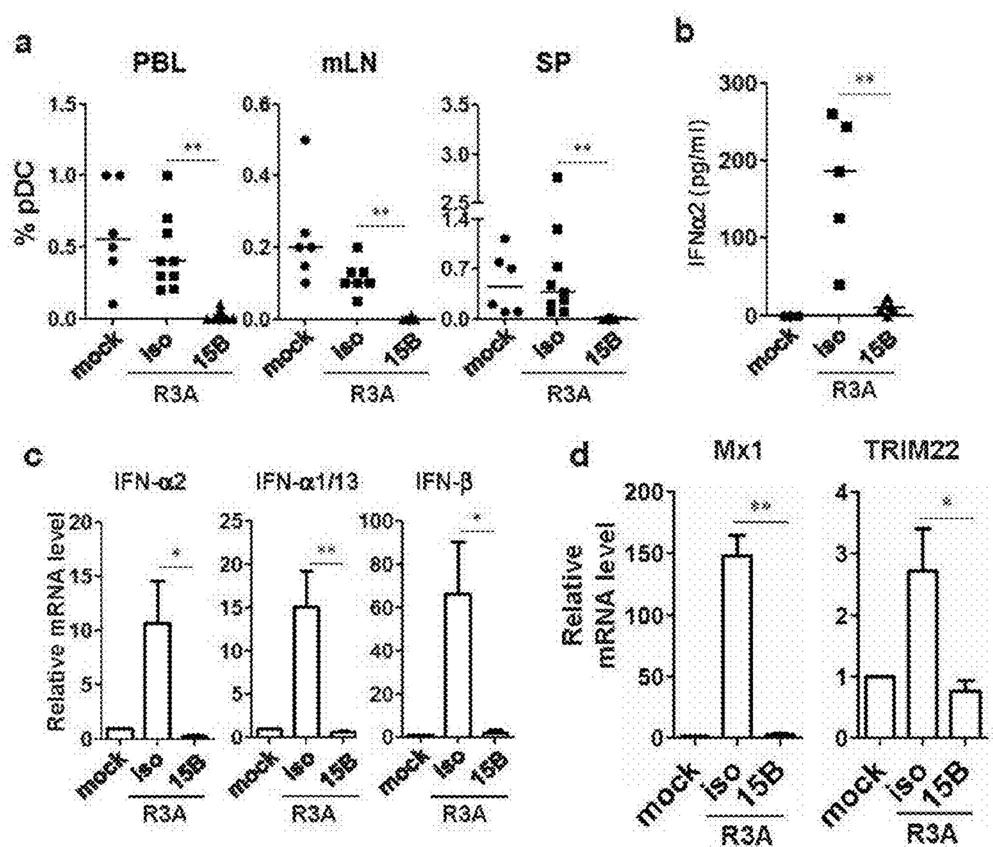

To test the roles of pDC during early primary HIV-1 infection, 15B and isotype control antibodies were injected into humanized mice on −5, −3 and −1 days before infection, and the mice infected with R3A, a highly pathogenic, CCR5- and CXCR4-dual tropic HIV-1 strain (Meissner et al., *Virology* 328:74 (2004); Sivaraman et al, *J. Virol.* 83:11715 (2009)). The infected mice were injected with 15B or control antibody on 3 and 6 days post-infection. It was found that pDC remained depleted in blood and lymphoid organs of the infected mice (FIG. 10*a*), when terminated on 8 days post-infection. Interestingly, the plasma IFN-I level was significantly abolished by pDC depletion in HIV-1 infected mice (FIG. 10*b*). The induction of different subtypes of human IFN-I was also abolished at RNA level by real time PCR (FIG. 10*c*). In addition, the upregulation of ISGs such as Mx1, TR1M22 was also blocked (FIG. 10*d*). These data demonstrate that pDCs are the major, if not the only, IFN-I producing cells in vivo during early HIV-1 infection in humanized mice.

Figures 11A, 11B, 11C, 11D, 11E:
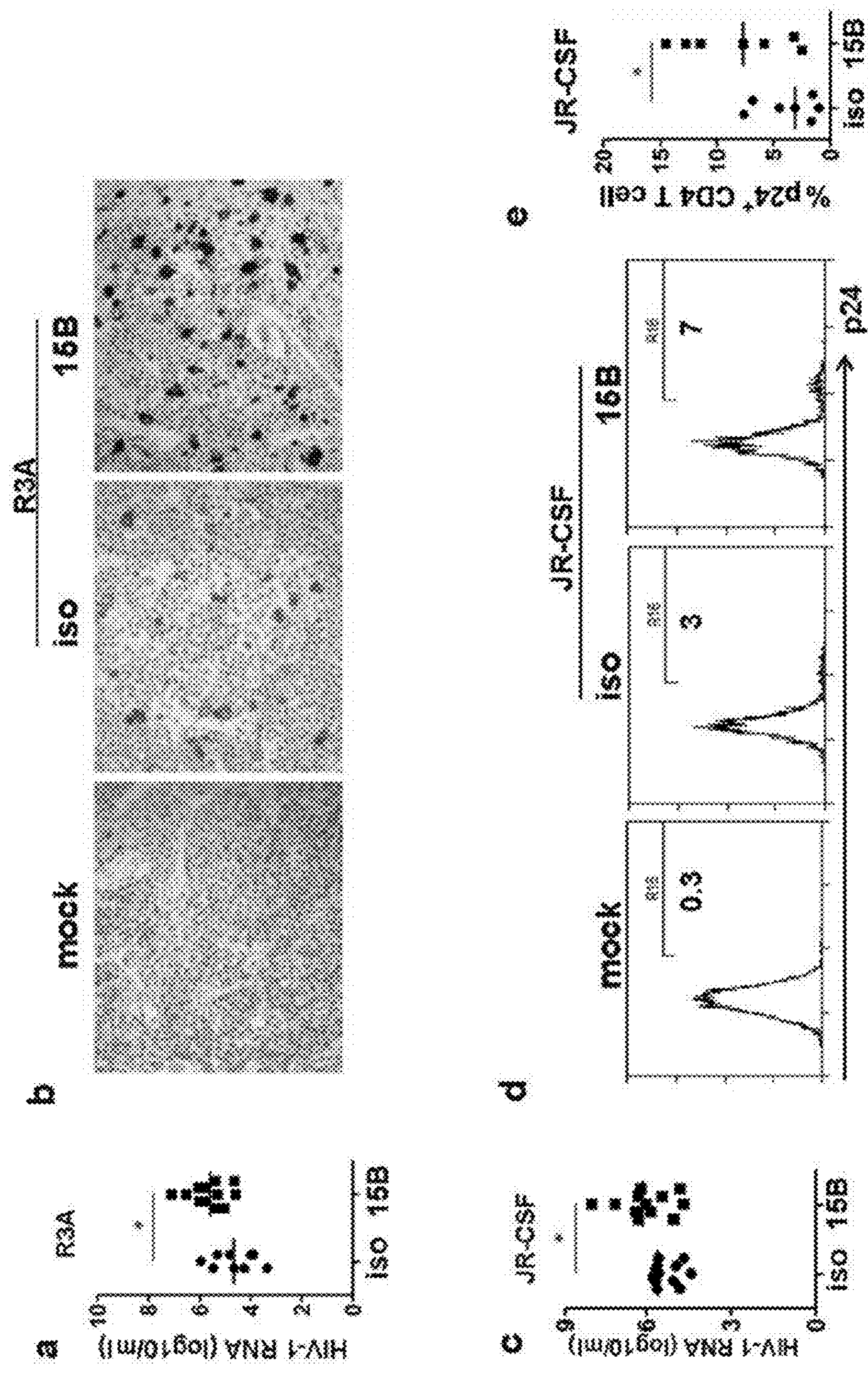

Consistent with the antiviral activity of IFN-I, pDC depletion led to elevated HIV-1 replication in vivo. The average plasma viremia was increased about 10-fold ($p<0.01$) comparing with control antibody treated mice (FIG. 11*a*). The experiment was repeated with the less pathogenic, CCR5 tropic HIV-1 JR-CSF. Similar to R3A infection, JR-CSF replication was also increased about 5-fold in pDC-depleted mice (FIG. 11*c*). The increase of viral replication was further confirmed by immunohistochemistry (FIG. 11*b*) or flow cytometry (FIGS. 11*d,e*) for HIV p24 protein positive cells in human cells from spleens.

Figures 12A, 12B, 12C, 12D:
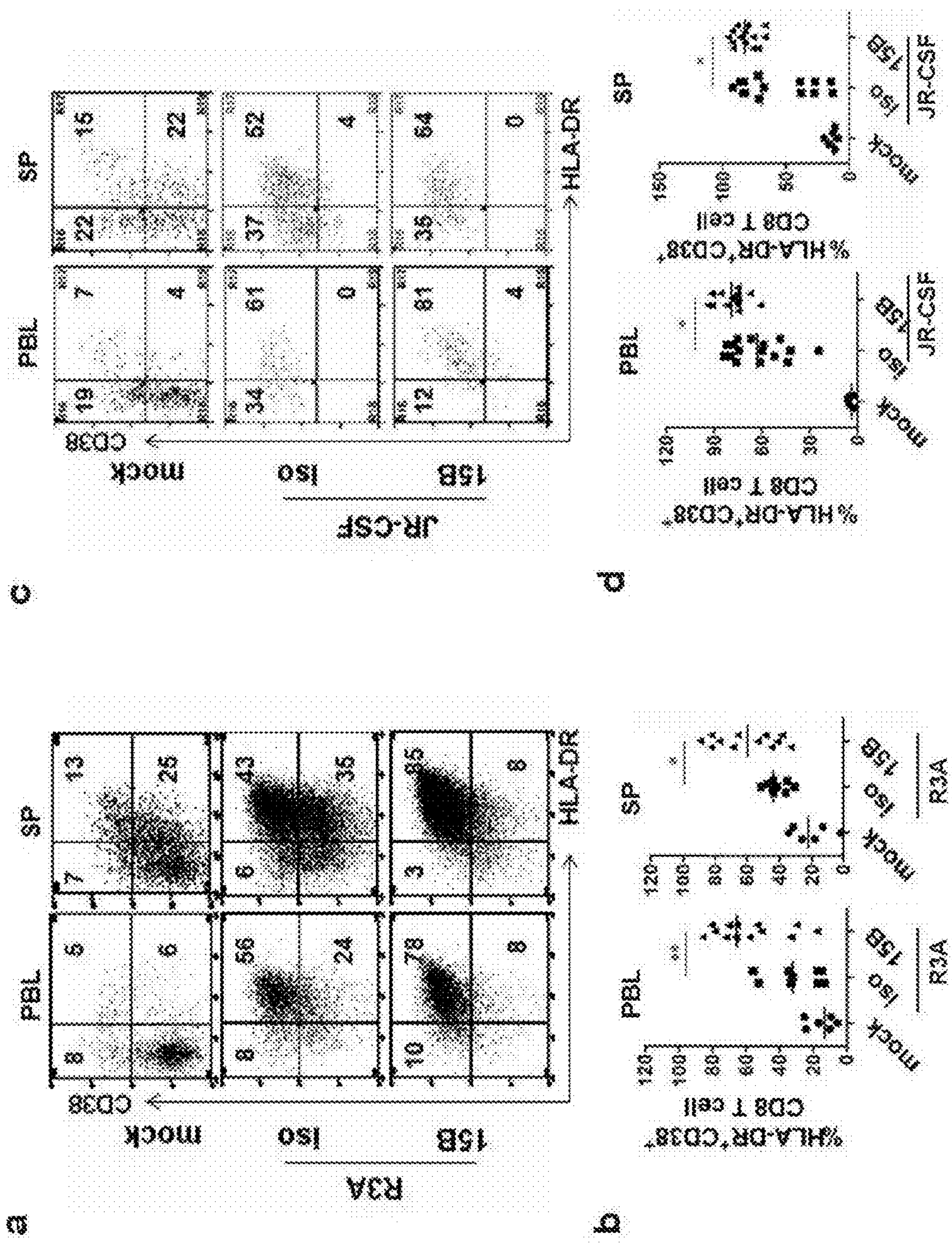

HIV-1 infection induces generalized immune activation (Lane et al., *N. Engl. J. Med.* 309:453 (1983); Ascher et al., *Clin. Exp. Immunol.* 73:165 (1988)), which is proposed to contribute to HIV-1 diseases progression (Lane et al., *N. Engl. J. Med.* 309:453 (1983); Ascher et al., *Clin. Exp. Immunol.* 73:165 (1988); Grossman et al., *Clin. Immunol. Immunopathol.* 69:123 (1993); Giorgi et al., *J. Acquir. Immune Defic. Syndr.* 6:904 (1993); Bosinger et al., *Curr. Opin. HIVAIDS* 6:411 (2011); Moir et al., *Annu. Rev. Pathol.* 6:223 (2011)). Induction of IFN-I and pDC activation have been hypothesized to contribute to the immune activation both in HIV-infected patients and in SIV-infected rhesus monkeys (Buimovici-Klein et al., *Lancet* 2:344 (1983); Buimovici-Klein et al., *AIDS Res.* 2:99-108 (1986); Meier et al., *Nature Medicine* 15:955 (2009); Harris et al., *J. Virol.* 84:7886 (2010); Campillo-Gimenez et al., *J. Virol.* 84:1838 (2010); Bosinger et al., *Curr. Opin. HIVAIDS* 6:411 (2011); Kwa et al., *Blood* 118:2763 (2011); Manches et al., *Proc. Natl. Acad. Sci. USA* 109:14122 (2012); Manches et al., *J. Clin. Invest.* 118:3431 (2008)). However, instead of decreasing T cell activation, a further increase of T cell activation (CD38+DR+) was observed in both blood and lymphoid organs in pDC-depleted mice infected with either R3A (FIGS. 12*a,b*) or JR-CSF (FIGS. 12*c,d*). Interestingly, it was found that the CD8 T cell activation level was correlated with viral load in pDC-depleted mice (FIG. 13). Thus, HIV-1 may also directly lead to the T-cell activation in the absence of INF-I.

Figures 14A, 14B, 14C, 14D, 14E:
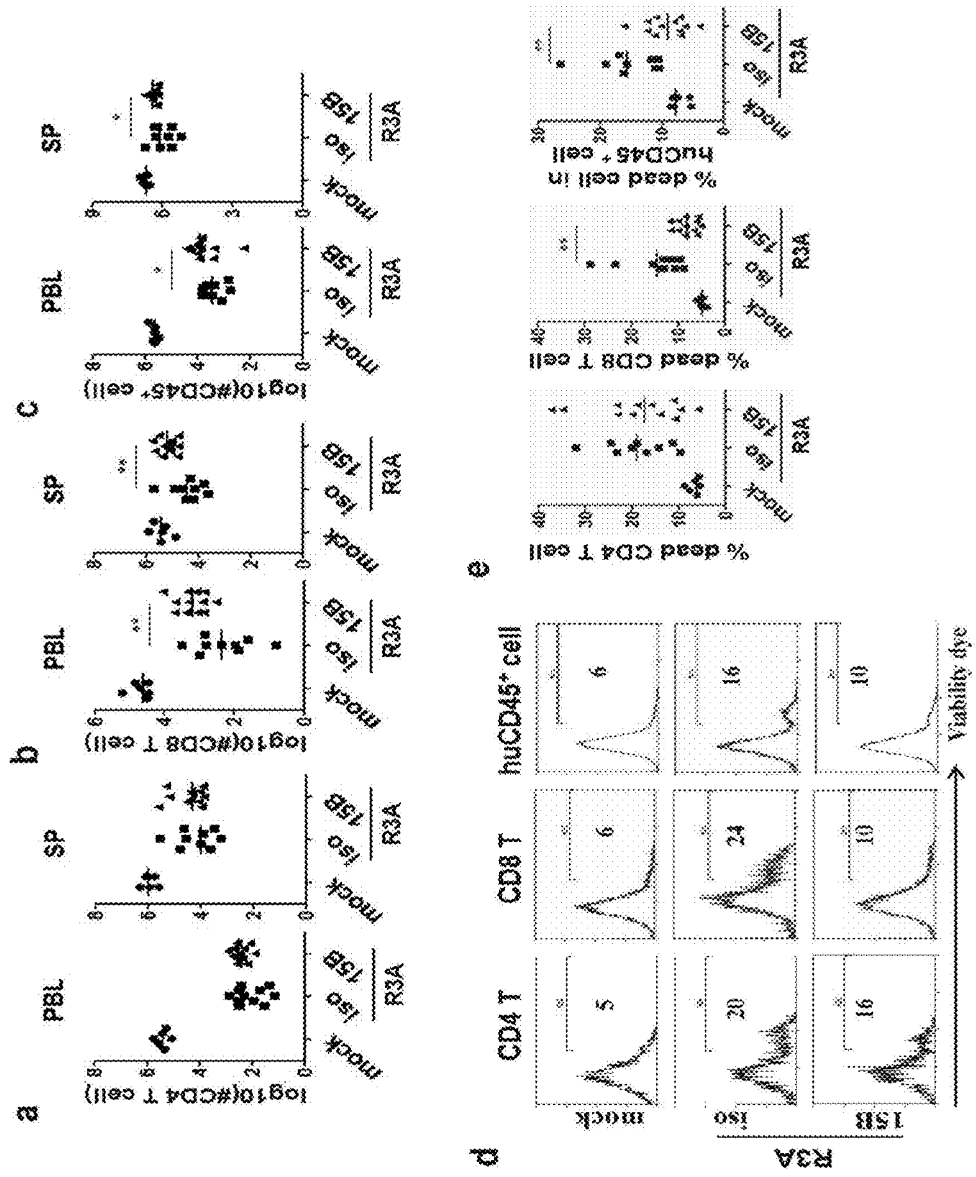

However, despite the increased HIV-R3A viral replication, the absolute numbers of human $CD4^+$ T cell in blood and spleen were comparable to those of control antibody treated mice (FIG. 14*a*). More surprisingly, $CD8^+$ cells of pDC depleted mice increased significantly compared with control antibody treated animals (FIG. 14*b*). Total human $CD45^+$ leukocytes were also preserved in blood and spleen (FIG. 14*c*), and this is correlated with decreased cell death of total CD45+ or CD8 T cells (FIGS. 14*d,e*). Similar findings were observed in JR-CSF infected mice, although only low levels of human $CD4^+$, $CD8^+$ T cells and total human leukocytes and depletion occurred at 3 weeks post-infection (FIG. 15).

EXAMPLE 5

Figures 16A, 16B, 16C, 16D, 16E, 16F, 16G:
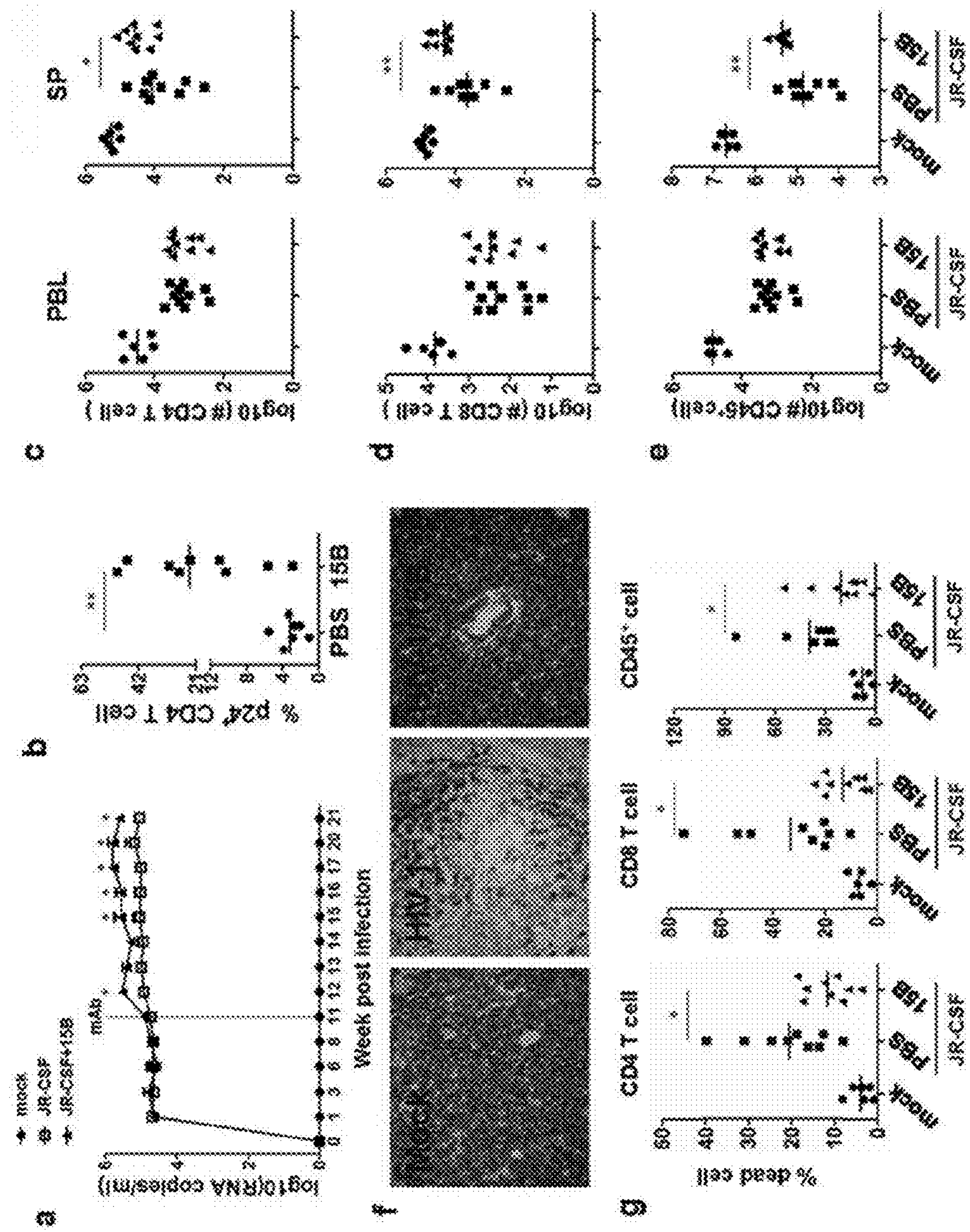
Figures 17A, 17B, 17C, 17D:
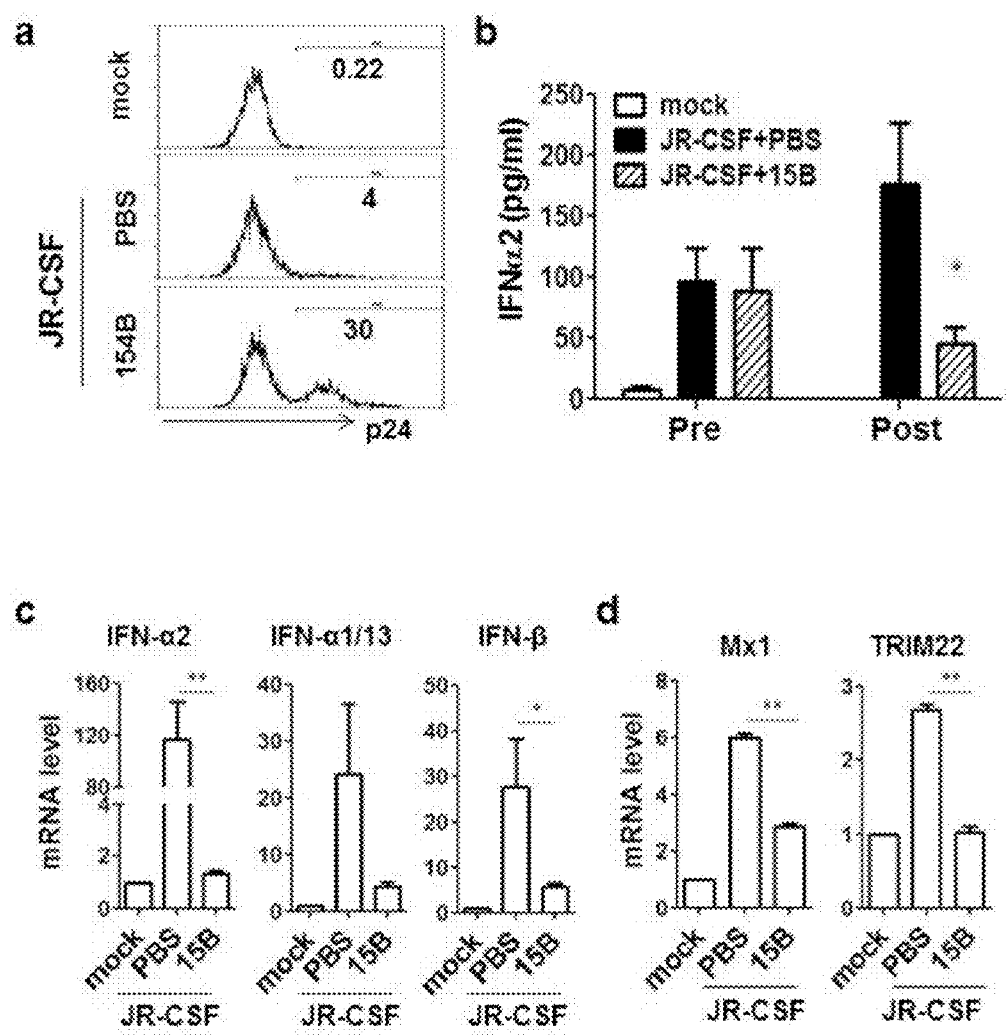
Figures 17E, 17F:
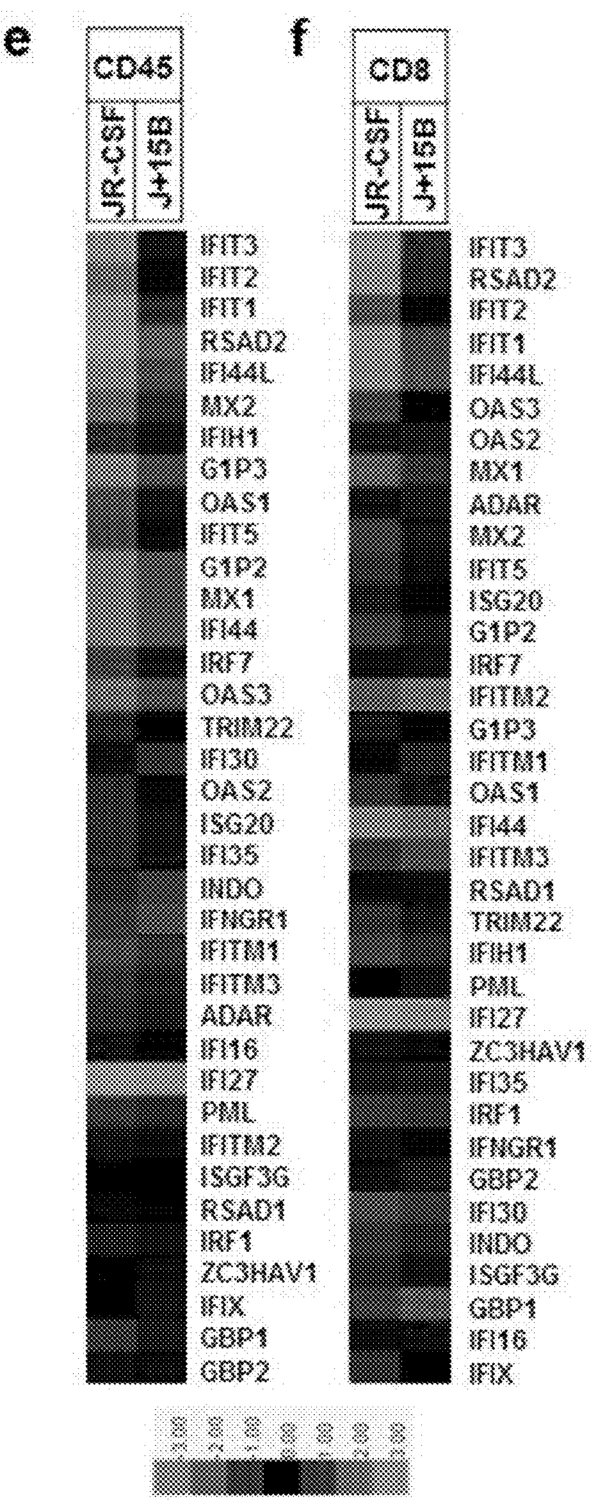

Role of Plasmacytoid Dendritic Cells in Chronic HIV-1 Infection pDC depletion was performed in humanized mice with established persistent HIV-1 infection. Humanized mice were infected with JR-CSF for 11 weeks; 15B was then applied to deplete pDCs. In agreement with the data from pre-infection pDC depletion, an increased viremia was observed that persisted for 10 weeks until termination (FIG. 16*a*). The percentage of HIV infected cells (HIV-1 p24 positive) also increased (FIG. 16*b*, FIG. 17*a*). Induction of plasma IFN-α2 was decreased significantly in the pDC-depleted mice (FIG. 17*b*). The diminished induction of different IFN-1 subtypes (FIG. 17*c*) and ISGs (FIG. 17*d*) at RNA level in human leukocytes in spleen were also evidenced by real-time PCR assay and cDNA array (FIGS. 17*e,f*). These data suggest that pDC are still the major INF-I producing cells during HIV-1 chronic infection in vivo.

In spite of the persistent higher viremia during those 10 weeks of pDC depletion, human $CD4^+$ T-cell numbers increased significantly in the spleen, comparing to the control group (FIG. 16*c*, $p<0.05$). In addition, human CD8 T cell and $CD45^+$ leukocyte numbers were also increased (FIGS. 16*d,e*, $p<0.01$). Interestingly, human CD4, CD8 T cells and total CD45+ leukocytes were not significantly rescued in the blood (FIGS. 16*c-e*). The increase of human CD45+ cells was also evidenced by CD45 immunohistochemistry stain of spleen sections (FIG. 16*f*). Accordingly, pDC depletion significantly reduced the percentage of dead/dying cells in T cells and total human $CD45^+$ cells in the spleen (FIG. 16*g*). Therefore, during chronic HIV-1 infection, pDC still play both a role in suppressing viral replication and enhancing HIV-induced immunopathogenesis.

The role of pDC in chronic virus infections such as HIV-1 remains controversial, due to the correlative studies performed in human patients or in SIV-infected monkeys (Cervantes-Barragan et al., *Proc. Natl. Acad. Sci, USA* 109:3012 (2012); Riviere et al., *J. Exp. Med.* 152:633 (1980); Wang et al., *Cell Host Microbe* 11:631 (2012)). Here it is reported that, by depleting pDC specifically with a novel antibody before or during HIV-1 infection, pDC are the major IFN-1 producing cells during HIV infection in vivo. It is reported that pDC play a dual role during HIV-1 infection and pathogenesis: they produce IFN-I to inhibit HIV-1 replication, but enhance HIV-1 pathogenesis by promoting death of human leukocytes including human CD4 and CD8 T cells. The residual IFN-I expression after 15B mAb treatment during persistent HIV-1 infection may be due to residual pDC in the bone marrow, although the contribution of other cells types cannot be excluded (Lepelley et al., *PLoS Pathogens* 7:e1001284 (2011)).

It is reported that pDC may contribute to HIV induced immune activation and subsequent immunopathogenesis. The anti-malaria drug chloroquine inhibits IFN-I production by pDC in vitro (Beignon et al., *J. Clin. Invest.* 115:3265 (2005)) and seems to rescue human T cells in HIV-1 infected patients, correlated with reduced immune activation (Murray et al., *J. Virol.* 84:12082 (2010); Piconi et al., *Blood* 118:3263 (2011)). Interestingly, HIV-activated pDCs also induce regulatory T cells (Tregs) through an indoleamine 2,3-dioxygenase (IDO)-dependent mechanism (Manches et al., *Proc. Natl. Acad. Sci. USA* 109:14122 (2012); Manches et al., *J. Clin. Invest.* 118:3431 (2008)). In this report, an increase of T-cell activation by pDC depletion was observed, probably due to the increased viral replication via a pDC/IFN-1 independent mechanism. A recent report shows that a TLR7 and TLR9 antagonist that could inhibit activation of pDC isolated from Rhesus monkeys did not significantly change plasma IFN-1 level and ISG expression in SIV infected monkeys, probably due to its incomplete inhibition of pDC in vivo or to the high level activation of mDC and macrophages (Kader et al., *PLoS Pathogens* 9:e1003530 (2013)). Thus, the relative roles of pDC and HIV-1 replication, as well as other immune cells, in immune activation need to be further investigated.

Repeated administrations of TLR7 ligands in mice induce AIDS-like lymphopenia, with reduced $CD4^+$ T cells, $CD8^+$ T cells and B cells (Baenziger et al., *Blood* 113:377 (2009)). It is reported that IFN-1 triggers proapoptotic and antiproliferative effect on T cells (Tanabe et al., *J. Immunol.* 174:609 (2005)), and activation of Stat4 by TCR signaling could overcome its STAT1-dependent inhibition of T cells proliferation (Gil et al., *Blood* 120:3718 (2012)). Similarly, TLR7 and TLR9 antagonist DV056-treated macaques show a significant increase in proliferating memory $CD4^+$ and $CD8^+$ T cells in blood (Kader et al., *PLoS Pathogens* 9:e1003530 (2013)). Consistently, it was found that pDC depletion not only rescued $CD4^+$ T cells but also total $CD45^+$ leukocytes and CD8 T cells. It is proposed that pDC may contribute to HIV immunopathogenesis by both inducing abnormal immune activation and by promoting depletion of human immune cells.

Recent reports also show that blocking IFN-I signaling during LCMV persistent infection could improve antiviral T cell response and accelerate clearance of chronic LCMV infection via an IL-10-dependent mechanisms (Wilson et al., *Science* 340:202 (2013); Teijaro et al., *Science* 340:207 (2013)). Similar findings were seen in our HIV-1 infection model, as the enhanced levels of CD8 T cells and IFNγ were correlated with pDC depletion and blocking of IFN-I induction. However, pDC-depletion did not seem to affect IL-10 expression in humanized mice, likely due to the elevated levels of HIV-1 replication. In HAART-treated HIV patients, a significant fraction fail to show reduced immune activation and efficient immune reconstitution even with efficient virological responses (Aiuti et al., *AIDS Rev.* 8:88 (2006); Gaardbo et al., *Clin. Dev. Immunol.* 2012:670957 (2012); Zhang et al., *Aids* 27:1283 (2013)). Persistent pDC activation and IFN-I induction may play a role in such immune no-responder patients. It is proposed that inhibition or depletion of pDC during HAART in HIV-1 chronic infection may provide an effective treatment to preserve human immune cells in HIV-1 infected patients.

EXAMPLE 6

Depletion of Plasmacytoid Dendritic Cells in Humanized Mice

Further screening of anti-BDCA2 (CD303) monoclonal antibodies identified another antibody (12B) that specifically depletes human pDC in lymphoid organs of humanized mice. After 12B injection, human pDC in CD45$^+$ leukocytes was greatly reduced in spleen (FIG. 20). As controls, human T and myeloid dendritic cells were not perturbed by 12B injection (FIG. 20).

The foregoing is illustrative of the present invention, and is not to be construed as limiting thereof. The invention is defined by the following claims, with equivalents of the claims to be included therein.

That which is claimed is:

1. A method of depleting plasmacytoid dendritic cells (pDC) in a subject, comprising delivering to the subject an effective amount of an antibody or a fragment thereof that specifically binds to blood dendritic cell antigen-2 (BDCA2) and depletes pDC, thereby depleting pDC;

wherein the antibody or a fragment thereof comprises a heavy chain variable region comprising the amino acid sequence of SEQ ID NO:2 or SEQ ID NO:6 and/or the antibody or a fragment thereof comprises a light chain variable region comprising the amino acid sequence of SEQ ID NO:4 or SEQ ED NO:8.

2. The method of claim 1, wherein the BDCA2 is human BDCA2.

3. The method of claim 1, wherein the antibody or a fragment thereof is a monoclonal antibody or fragment or derivative thereof.

4. The method of claim 3, wherein the monoclonal antibody or a fragment thereof specifically binds the epitope IQNLKRNSSYFLGLSDPGGR, (SEQ ID NO:9) or a fragment thereof of at least 5 contiguous amino acids.

5. The method of claim 3, wherein the monoclonal antibody or a fragment thereof comprises a heavy chain variable region comprising the amino acid sequence of SEQ ID NO:2 and a light chain variable region comprising the amino acid sequence of SEQ ID NO:4.

6. The method of claim 3, wherein the monoclonal antibody or a fragment thereof comprises a heavy chain variable region comprising, the amino acid sequence of SEQ ID) NO:6 and a light chain variable region comprising the amino acid sequence of SEQ ID NO:8.

7. The method of claim 3, wherein the monoclonal antibody or a fragment thereof is a chimeric antibody or a fragment thereof.

8. The method of claim 3, wherein the monoclonal antibody or a fragment thereof is a humanized antibody or a fragment thereof.

9. A method of treating a disorder associated with pDC in a subject in need thereof, comprising delivering to the subject a therapeutically effective amount an antibody or a fragment thereof that specifically binds to BDCA2 and depletes pDC, thereby treating the disorder;

wherein the disorder is human immunodeficiency virus infection or an autoimmune disease; and wherein the antibody or a fragment thereof comprises a heavy chain variable region comprising the amino acid sequence of SEQ ID NO:2 or SEQ ID NO:6; and/or the antibody or a fragment thereof comprises a light chain variable region comprising the amino acid sequence of SEQ ID NO:4 or SEQ ID NO:8.

10. The method of claim 9, wherein the disorder is human immunodeficiency virus infection.

11. A method of depleting pDC in a mixed population of cells, comprising delivering to the mixed population of cells an effective amount of an antibody or a fragment thereof that specifically binds to BDCA2 and depletes pDC, thereby depleting pDC in the mixed population of cells;

wherein the antibody or a fragment thereof comprises a heavy chain variable region comprising the amino acid sequence of SEQ ID NO:2 or SEQ ID NO:6; and/or the antibody or a fragment thereof comprises a light chain variable region comprising the amino acid sequence of SEQ ID NO;4 or SEQ ID NO:8.

* * * * *

UNITED STATES PATENT AND TRADEMARK OFFICE

CERTIFICATE OF CORRECTION

PATENT NO. : 9,670,283 B2
APPLICATION NO. : 15/092275
DATED : June 6, 2017
INVENTOR(S) : Su It is certified that error appears in the above-identified patent and that said Letters Patent is hereby corrected as shown below:

In the Specification

Column 1, Line 62: Please correct "virus (SN)" to read -- virus (SIV) --

Column 2, Line 36: Please correct "depletes pXDC" to read -- depletes pDC --
Line 57: Please correct "of IFN-α2" to read -- of IFN-a2 --

Column 3, Line 24: Please correct "mice (n=-10)." to read -- mice (n=10). --
Line 58: Please correct "CD14+ cell" to read -- CD11c+ cell --

Column 4, Line 45: Please correct "cell (CD34CD8-)" to read -- cell (CD3+CD8-) --

Column 13, Line 28: Please correct "SEQ ID) NO:3" to read -- SEQ ID NO:3 --

Column 23, Line 5: Please correct "GAPDH gene 59" to read -- GAPDH gene [59] --
Line 28: Please correct "with CD4+ T-cell" to read -- with $CD4^+$ T-cell --
Line 49: Please correct "ISO genes" to read -- ISG genes --

In the Claims

Column 45, Claim 6, Line 66: Please correct "ID) NO:6" to read -- ID NO:6 --

Column 47, Claim 11, Line 6: Please correct "SEQ ID NO;4" to read -- SEQ ID NO:4 --

Signed and Sealed this
Sixth Day of February, 2018

Joseph Matal

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 9

<210> SEQ ID NO 1
<211> LENGTH: 1416
<212> TYPE: DNA
<213> ORGANISM: Artificial
<220> FEATURE:
<223> OTHER INFORMATION: Heavy chain coding sequence for monoclonal antibody from hybridoma cell line 15B
<220> FEATURE:
<221> NAME/KEY: CDS
<222> LOCATION: (1)..(1413)

<400> SEQUENCE: 1 atg gga tgg aac tgg atc ttt att tta atc ctg tca gta act aca ggt 48
Met Gly Trp Asn Trp Ile Phe Ile Leu Ile Leu Ser Val Thr Thr Gly
1 5 10 15 gtc cac tct gag gtc caa ctg cag cag tct gga cct gag ctg gtg aag 96
Val His Ser Glu Val Gln Leu Gln Gln Ser Gly Pro Glu Leu Val Lys
20 25 30 cct ggg gct tca gtg aag ata tcc tgc aag gct tct ggt tac tca ttc 144
Pro Gly Ala Ser Val Lys Ile Ser Cys Lys Ala Ser Gly Tyr Ser Phe
35 40 45 act gtc tac tac atg cac tgg gtg aag caa agt cct gaa aat agt ctt 192
Thr Val Tyr Tyr Met His Trp Val Lys Gln Ser Pro Glu Asn Ser Leu
50 55 60 gag tgg att gga gag att aat cct agc act ggg ggt act agc tac aac 240
Glu Trp Ile Gly Glu Ile Asn Pro Ser Thr Gly Gly Thr Ser Tyr Asn
65 70 75 80 cag aag ttc aag ggc aag gcc aca tta act gta gat gaa tcc tcc agc 288
Gln Lys Phe Lys Gly Lys Ala Thr Leu Thr Val Asp Glu Ser Ser Ser
85 90 95 aca gcc tac atg cag ctc aag agc ctg aca tct gaa gag tct gca gtc 336
Thr Ala Tyr Met Gln Leu Lys Ser Leu Thr Ser Glu Glu Ser Ala Val
100 105 110 tat tac tgt aca acc ccc tac tat agg tac gag ggg gac tgg tac ttc 384
Tyr Tyr Cys Thr Thr Pro Tyr Tyr Arg Tyr Glu Gly Asp Trp Tyr Phe
115 120 125 gat gtc tgg ggc gca ggg acc acg gtc acc gtc tcc tca gct aaa aca 432
Asp Val Trp Gly Ala Gly Thr Thr Val Thr Val Ser Ser Ala Lys Thr
130 135 140 aca gcc cca tcg gtc tat cca ctg gcc cct gtg tgt gga gat aca act 480
Thr Ala Pro Ser Val Tyr Pro Leu Ala Pro Val Cys Gly Asp Thr Thr
145 150 155 160 ggc tcc tcg gtg act cta gga tgc ctg gtc aag ggt tat ttc cct gag 528
Gly Ser Ser Val Thr Leu Gly Cys Leu Val Lys Gly Tyr Phe Pro Glu
165 170 175 cca gtg acc ttg acc tgg aac tct gga tcc ctg tcc agt ggt gtg cac 576
Pro Val Thr Leu Thr Trp Asn Ser Gly Ser Leu Ser Ser Gly Val His
180 185 190 acc ttc cca gct gtc ctg cag tct gac ctc tac acc ctc agc agc tca 624
Thr Phe Pro Ala Val Leu Gln Ser Asp Leu Tyr Thr Leu Ser Ser Ser
195 200 205 gtg act gta acc tcg agc acc tgg ccc agc cag tcc atc acc tgc aat 672
Val Thr Val Thr Ser Ser Thr Trp Pro Ser Gln Ser Ile Thr Cys Asn
210 215 220

```
gtg gcc cac ccg gca agc agc acc aag gtg gac aag aaa att gag ccc      720
Val Ala His Pro Ala Ser Ser Thr Lys Val Asp Lys Lys Ile Glu Pro
225                 230                 235                 240

aga ggg ccc aca atc aag ccc tgt cct cca tgc aaa tgc cca gca cct      768
Arg Gly Pro Thr Ile Lys Pro Cys Pro Pro Cys Lys Cys Pro Ala Pro
                245                 250                 255

aac ctc ttg ggt gga cca tcc gtc ttc atc ttc cct cca aag atc aag      816
Asn Leu Leu Gly Gly Pro Ser Val Phe Ile Phe Pro Pro Lys Ile Lys
            260                 265                 270

gat gta ctc atg atc tcc ctg agc ccc ata gtc aca tgt gtg gtg gtg      864
Asp Val Leu Met Ile Ser Leu Ser Pro Ile Val Thr Cys Val Val Val
        275                 280                 285

gat gtg agc gag gat gac cca gat gtc cag atc agc tgg ttt gtg aac      912
Asp Val Ser Glu Asp Asp Pro Asp Val Gln Ile Ser Trp Phe Val Asn
    290                 295                 300

aac gtg gaa gta cac aca gct cag aca caa acc cat aga gag gat tac      960
Asn Val Glu Val His Thr Ala Gln Thr Gln Thr His Arg Glu Asp Tyr
305                 310                 315                 320

aac agt act ctc cgg gtg gtc agt gcc ctc ccc atc cag cac cag gac     1008
Asn Ser Thr Leu Arg Val Val Ser Ala Leu Pro Ile Gln His Gln Asp
                325                 330                 335

tgg atg agt ggc aag gag ttc aaa tgc aag gtc aac aac aaa gac ctc     1056
Trp Met Ser Gly Lys Glu Phe Lys Cys Lys Val Asn Asn Lys Asp Leu
            340                 345                 350

cca gcg ccc atc gag aga acc atc tca aaa ccc aaa ggg tca gta aga     1104
Pro Ala Pro Ile Glu Arg Thr Ile Ser Lys Pro Lys Gly Ser Val Arg
        355                 360                 365

gct cca cag gta tat gtc ttg cct cca cca gaa gaa gag atg act aag     1152
Ala Pro Gln Val Tyr Val Leu Pro Pro Pro Glu Glu Glu Met Thr Lys
    370                 375                 380

aaa cag gtc act ctg acc tgc atg gtc aca gac ttc atg cct gaa gac     1200
Lys Gln Val Thr Leu Thr Cys Met Val Thr Asp Phe Met Pro Glu Asp
385                 390                 395                 400

att tac gtg gag tgg acc aac aac ggg aaa aca gag cta aac tac aag     1248
Ile Tyr Val Glu Trp Thr Asn Asn Gly Lys Thr Glu Leu Asn Tyr Lys
                405                 410                 415

aac act gaa cca gtc ctg gac tct gat ggt tct tac ttc atg tac agc     1296
Asn Thr Glu Pro Val Leu Asp Ser Asp Gly Ser Tyr Phe Met Tyr Ser
            420                 425                 430

aag ctg aga gtg gaa aag aag aac tgg gtg gaa aga aat agc tac tcc     1344
Lys Leu Arg Val Glu Lys Lys Asn Trp Val Glu Arg Asn Ser Tyr Ser
        435                 440                 445

tgt tca gtg gtc cac gag ggt ctg cac aat cac cac acg act aag agc     1392
Cys Ser Val Val His Glu Gly Leu His Asn His His Thr Thr Lys Ser
    450                 455                 460

ttc tcc cgg act ccg ggt aaa taa                                     1416
Phe Ser Arg Thr Pro Gly Lys
465                 470
```

<210> SEQ ID NO 2
<211> LENGTH: 471
<212> TYPE: PRT
<213> ORGANISM: Artificial
<220> FEATURE:
<223> OTHER INFORMATION: Synthetic Construct

<400> SEQUENCE: 2

```
Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30
```

```
Pro Gly Ala Ser Val Lys Ile Ser Cys Lys Ala Ser Gly Tyr Ser Phe
        35                  40                  45

Thr Val Tyr Tyr Met His Trp Val Lys Gln Ser Pro Glu Asn Ser Leu
    50                  55                  60

Glu Trp Ile Gly Glu Ile Asn Pro Ser Thr Gly Gly Thr Ser Tyr Asn
65                  70                  75                  80

Gln Lys Phe Lys Gly Lys Ala Thr Leu Thr Val Asp Glu Ser Ser Ser
                85                  90                  95

Thr Ala Tyr Met Gln Leu Lys Ser Leu Thr Ser Glu Glu Ser Ala Val
            100                 105                 110

Tyr Tyr Cys Thr Thr Pro Tyr Tyr Arg Tyr Glu Gly Asp Trp Tyr Phe
        115                 120                 125

Asp Val Trp Gly Ala Gly Thr Thr Val Thr Val Ser Ser Ala Lys Thr
    130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Thr Ser Ser Thr Trp Pro Ser Gln Ser Ile Thr Cys Asn
    210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
            260                 265                 270

Asp Val Leu Met Ile Ser Leu Ser Pro Ile Val Thr Cys Val Val Val
        275                 280                 285

Asp Val Ser Glu Asp Asp Pro Asp Val Gln Ile Ser Trp Phe Val Asn
    290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Pro Lys Gly Ser Val Arg
        355                 360                 365

Ala Pro Gln Val Tyr Val Leu Pro Pro Pro Glu Glu Glu Met Thr Lys
    370                 375                 380

Lys Gln Val Thr Leu Thr Cys Met Val Thr Asp Phe Met Pro Glu Asp
385                 390                 395                 400

Ile Tyr Val Glu Trp Thr Asn Asn Gly Lys Thr Glu Leu Asn Tyr Lys
                405                 410                 415

Asn Thr Glu Pro Val Leu Asp Ser Asp Gly Ser Tyr Phe Met Tyr Ser
            420                 425                 430

Lys Leu Arg Val Glu Lys Lys Asn Trp Val Glu Arg Asn Ser Tyr Ser
        435                 440                 445
```

```
Cys Ser Val Val His Glu Gly Leu His Asn His His Thr Thr Lys Ser
    450                 455                 460

Phe Ser Arg Thr Pro Gly Lys
465                 470


<210> SEQ ID NO 3
<211> LENGTH: 708
<212> TYPE: DNA
<213> ORGANISM: Artificial
<220> FEATURE:
<223> OTHER INFORMATION: Light chain coding sequence for monoclonal
      antibody from hybridoma cell line 15B
<220> FEATURE:
<221> NAME/KEY: CDS
<222> LOCATION: (1)..(705)

<400> SEQUENCE: 3

atg cat ttt caa gtg cag att ttc agc ttc ctg cta atc agt gcc tca       48
Met His Phe Gln Val Gln Ile Phe Ser Phe Leu Leu Ile Ser Ala Ser
1               5                   10                  15

gtc ata atg tcc aga gga caa att gtt ctc acc cag tct cca gca atc       96
Val Ile Met Ser Arg Gly Gln Ile Val Leu Thr Gln Ser Pro Ala Ile
            20                  25                  30

atg tct gca tct cca ggg gag aag gtc acc ata acc tgc agt gcc agc      144
Met Ser Ala Ser Pro Gly Glu Lys Val Thr Ile Thr Cys Ser Ala Ser
        35                  40                  45

tca agt gta agt tac atg cac tgg ttc cag cag aag cca ggc act tct      192
Ser Ser Val Ser Tyr Met His Trp Phe Gln Gln Lys Pro Gly Thr Ser
    50                  55                  60

ccc aaa ctc tgg att tat agc aca tcc aac ctg gct tct gga gtc cct      240
Pro Lys Leu Trp Ile Tyr Ser Thr Ser Asn Leu Ala Ser Gly Val Pro
65                  70                  75                  80

gct cgc ttc agt ggc agt gga tct ggg acc tct tac tct ctc aca atc      288
Ala Arg Phe Ser Gly Ser Gly Ser Gly Thr Ser Tyr Ser Leu Thr Ile
                85                  90                  95

agc cga atg gag gct gaa gat gct gcc act tat tac tgc cac caa agg      336
Ser Arg Met Glu Ala Glu Asp Ala Ala Thr Tyr Tyr Cys His Gln Arg
            100                 105                 110

agt agt tac cca cgg acg ttc ggt gga ggc acc aag ctg gaa atc aga      384
Ser Ser Tyr Pro Arg Thr Phe Gly Gly Gly Thr Lys Leu Glu Ile Arg
        115                 120                 125

cgg gct gat gct gca cca act gta tcc atc ttc cca cca tcc agt gag      432
Arg Ala Asp Ala Ala Pro Thr Val Ser Ile Phe Pro Pro Ser Ser Glu
    130                 135                 140

cag tta aca tct gga ggt gcc tca gtc gtg tgc ttc ttg aac aac ttc      480
Gln Leu Thr Ser Gly Gly Ala Ser Val Val Cys Phe Leu Asn Asn Phe
145                 150                 155                 160

tac ccc aaa gac atc aat gtc aag tgg aag att gat ggc agt gaa cga      528
Tyr Pro Lys Asp Ile Asn Val Lys Trp Lys Ile Asp Gly Ser Glu Arg
                165                 170                 175

caa aat ggc gtc ctg aac agt tgg act gat cag gac agc aaa gac agc      576
Gln Asn Gly Val Leu Asn Ser Trp Thr Asp Gln Asp Ser Lys Asp Ser
            180                 185                 190

acc tac agc atg agc agc acc ctc acg ttg acc aag gac gag tat gaa      624
Thr Tyr Ser Met Ser Ser Thr Leu Thr Leu Thr Lys Asp Glu Tyr Glu
        195                 200                 205

cga cat aac agc tat acc tgt gag gcc act cac aag aca tca act tca      672
Arg His Asn Ser Tyr Thr Cys Glu Ala Thr His Lys Thr Ser Thr Ser
    210                 215                 220

ccc att gtc aag agc ttc aac agg aat gag tgt tag                      708
Pro Ile Val Lys Ser Phe Asn Arg Asn Glu Cys
225                 230                 235
```

```
<210> SEQ ID NO 4
<211> LENGTH: 235
<212> TYPE: PRT
<213> ORGANISM: Artificial
<220> FEATURE:
<223> OTHER INFORMATION: Synthetic Construct

<400> SEQUENCE: 4

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys His Gln Arg
            100                 105                 110

Ser Ser Tyr Pro Arg Thr Phe Gly Gly Gly Thr Lys Leu Glu Ile Arg
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 5
<211> LENGTH: 1404
<212> TYPE: DNA
<213> ORGANISM: Artificial
<220> FEATURE:
<223> OTHER INFORMATION: Heavy chain coding sequence for monoclonal
      antibody from hybridoma cell line 12B
<220> FEATURE:
<221> NAME/KEY: CDS
<222> LOCATION: (1)..(1401)

<400> SEQUENCE: 5

atg aac ttc ggg ttc agc ttg att ttc ctt gtc ctt gtt tta aaa ggt       48
Met Asn Phe Gly Phe Ser Leu Ile Phe Leu Val Leu Val Leu Lys Gly
1               5                   10                  15

gtc cag tgt gaa gtg aag ctg gtg gag tct ggg gga ggc tta gtg aag       96
Val Gln Cys Glu Val Lys Leu Val Glu Ser Gly Gly Gly Leu Val Lys
            20                  25                  30

cct gga ggg tcc ctg aaa ctc tcc tgt gca gcc tct gga ttc act ttc      144
```

```
Pro Gly Gly Ser Leu Lys Leu Ser Cys Ala Ala Ser Gly Phe Thr Phe
        35                  40                  45

agt acc atg tct tgg gtt cgc cag act cca gag aag agg ctg gag tgg      192
Ser Thr Met Ser Trp Val Arg Gln Thr Pro Glu Lys Arg Leu Glu Trp
    50                  55                  60

gtc gca tcc att agt agt ggt ggt agt act tac tat cca gac agt gtg      240
Val Ala Ser Ile Ser Ser Gly Gly Ser Thr Tyr Tyr Pro Asp Ser Val
65                  70                  75                  80

aag ggc cga ttc acc atc tcc aga gat aat gcc agg aac atc ctg tac      288
Lys Gly Arg Phe Thr Ile Ser Arg Asp Asn Ala Arg Asn Ile Leu Tyr
                85                  90                  95

ctg caa atg agc agt ctg agg tct gag gac acg gcc atg tat tac tgt      336
Leu Gln Met Ser Ser Leu Arg Ser Glu Asp Thr Ala Met Tyr Tyr Cys
            100                 105                 110

gca aga ccc tct tat gat ggt tac tcc tcc tgg ttt gct tac tgg ggc      384
Ala Arg Pro Ser Tyr Asp Gly Tyr Ser Ser Trp Phe Ala Tyr Trp Gly
        115                 120                 125

caa ggg act ctg gtc act gtc tct gca gcc aaa aca aca gcc cca tcg      432
Gln Gly Thr Leu Val Thr Val Ser Ala Ala Lys Thr Thr Ala Pro Ser
    130                 135                 140

gtc tat cca ctg gcc cct gtg tgt gga gat aca act ggc tcc tcg gtg      480
Val Tyr Pro Leu Ala Pro Val Cys Gly Asp Thr Thr Gly Ser Ser Val
145                 150                 155                 160

act cta gga tgc ctg gtc aag ggt tat ttc cct gag cca gtg acc ttg      528
Thr Leu Gly Cys Leu Val Lys Gly Tyr Phe Pro Glu Pro Val Thr Leu
                165                 170                 175

acc tgg aac tct gga tcc ctg tcc agt ggt gtg cac acc ttc cca gct      576
Thr Trp Asn Ser Gly Ser Leu Ser Ser Gly Val His Thr Phe Pro Ala
            180                 185                 190

gtc ctg cag tct gac ctc tac acc ctc agc agc tca gtg act gta acc      624
Val Leu Gln Ser Asp Leu Tyr Thr Leu Ser Ser Ser Val Thr Val Thr
        195                 200                 205

tcg agc acc tgg ccc agc cag tcc atc acc tgc aat gtg gcc cac ccg      672
Ser Ser Thr Trp Pro Ser Gln Ser Ile Thr Cys Asn Val Ala His Pro
    210                 215                 220

gca agc agc acc aag gtg gac aag aaa att gag ccc aga ggg ccc aca      720
Ala Ser Ser Thr Lys Val Asp Lys Lys Ile Glu Pro Arg Gly Pro Thr
225                 230                 235                 240

atc aag ccc tgt cct cca tgc aaa tgc cca gca cct aac ctc ttg ggt      768
Ile Lys Pro Cys Pro Pro Cys Lys Cys Pro Ala Pro Asn Leu Leu Gly
                245                 250                 255

gga cca tcc gtc ttc atc ttc cct cca aag atc aag gat gta ctc atg      816
Gly Pro Ser Val Phe Ile Phe Pro Pro Lys Ile Lys Asp Val Leu Met
            260                 265                 270

atc tcc ctg agc ccc ata gtc aca tgt gtg gtg gtg gat gtg agc gag      864
Ile Ser Leu Ser Pro Ile Val Thr Cys Val Val Val Asp Val Ser Glu
        275                 280                 285

gat gac cca gat gtc cag atc agc tgg ttt gtg aac aac gtg gaa gta      912
Asp Asp Pro Asp Val Gln Ile Ser Trp Phe Val Asn Asn Val Glu Val
    290                 295                 300

cac aca gct cag aca caa acc cat aga gag gat tac aac agt act ctc      960
His Thr Ala Gln Thr Gln Thr His Arg Glu Asp Tyr Asn Ser Thr Leu
305                 310                 315                 320

cgg gtg gtc agt gcc ctc ccc atc cag cac cag gac tgg atg agt ggc     1008
Arg Val Val Ser Ala Leu Pro Ile Gln His Gln Asp Trp Met Ser Gly
                325                 330                 335

aag gag ttc aaa tgc aag gtc aac aac aaa gac ctc cca gcg ccc atc     1056
Lys Glu Phe Lys Cys Lys Val Asn Asn Lys Asp Leu Pro Ala Pro Ile
            340                 345                 350
```

```
gag aga acc atc tca aaa ccc aaa ggg tca gta aga gct cca cag gta      1104
Glu Arg Thr Ile Ser Lys Pro Lys Gly Ser Val Arg Ala Pro Gln Val
        355                 360                 365

tat gtc ttg cct cca cca gaa gaa gag atg act aag aaa cag gtc act      1152
Tyr Val Leu Pro Pro Pro Glu Glu Glu Met Thr Lys Lys Gln Val Thr
    370                 375                 380

ctg acc tgc atg gtc aca gac ttc atg cct gaa gac att tac gtg gag      1200
Leu Thr Cys Met Val Thr Asp Phe Met Pro Glu Asp Ile Tyr Val Glu
385                 390                 395                 400

tgg acc aac aac ggg aaa aca gag cta aac tac aag aac act gaa cca      1248
Trp Thr Asn Asn Gly Lys Thr Glu Leu Asn Tyr Lys Asn Thr Glu Pro
                405                 410                 415

gtc ctg gac tct gat ggt tct tac ttc atg tac agc aag ctg aga gtg      1296
Val Leu Asp Ser Asp Gly Ser Tyr Phe Met Tyr Ser Lys Leu Arg Val
            420                 425                 430

gaa aag aag aac tgg gtg gaa aga aat agc tac tcc tgt tca gtg gtc      1344
Glu Lys Lys Asn Trp Val Glu Arg Asn Ser Tyr Ser Cys Ser Val Val
        435                 440                 445

cac gag ggt ctg cac aat cac cac acg act aag agc ttc tcc cgg act      1392
His Glu Gly Leu His Asn His His Thr Thr Lys Ser Phe Ser Arg Thr
    450                 455                 460

ccg ggt aaa taa                                                      1404
Pro Gly Lys
465


<210> SEQ ID NO 6
<211> LENGTH: 467
<212> TYPE: PRT
<213> ORGANISM: Artificial
<220> FEATURE:
<223> OTHER INFORMATION: Synthetic Construct

<400> SEQUENCE: 6

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Met Ser Trp Val Arg Gln Thr Pro Glu Lys Arg Leu Glu Trp
    50                  55                  60

Val Ala Ser Ile Ser Ser Gly Gly Ser Thr Tyr Tyr Pro Asp Ser Val
65                  70                  75                  80

Lys Gly Arg Phe Thr Ile Ser Arg Asp Asn Ala Arg Asn Ile Leu Tyr
                85                  90                  95

Leu Gln Met Ser Ser Leu Arg Ser Glu Asp Thr Ala Met Tyr Tyr Cys
            100                 105                 110

Ala Arg Pro Ser Tyr Asp Gly Tyr Ser Ser Trp Phe Ala Tyr Trp Gly
        115                 120                 125

Gln Gly Thr Leu Val Thr Val Ser Ala Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
```

```
        195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Val Asp Val Ser Glu
        275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
            340                 345                 350

Glu Arg Thr Ile Ser Lys Pro Lys Gly Ser Val Arg Ala Pro Gln Val
        355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
        435                 440                 445

His Glu Gly Leu His Asn His His Thr Thr Lys Ser Phe Ser Arg Thr
    450                 455                 460

Pro Gly Lys
465


<210> SEQ ID NO 7
<211> LENGTH: 717
<212> TYPE: DNA
<213> ORGANISM: Artificial
<220> FEATURE:
<223> OTHER INFORMATION: Light chain coding sequence for monoclonal
      antibody from hybridoma cell line 12B
<220> FEATURE:
<221> NAME/KEY: CDS
<222> LOCATION: (1)..(714)

<400> SEQUENCE: 7

atg gag aca gac aca atc ctg cta tgg gtg ctg ctg ctc tgg gtt cca       48
Met Glu Thr Asp Thr Ile Leu Leu Trp Val Leu Leu Leu Trp Val Pro
1               5                   10                  15

ggc tcc act ggt gac att gtg ctg acc caa tct cca gct tct ttg gct       96
Gly Ser Thr Gly Asp Ile Val Leu Thr Gln Ser Pro Ala Ser Leu Ala
            20                  25                  30

gtg tct cta ggg cag agg gcc acc atc tcc tgc aag gcc agc caa agt      144
Val Ser Leu Gly Gln Arg Ala Thr Ile Ser Cys Lys Ala Ser Gln Ser
        35                  40                  45
```

```
gtt gat tat gat ggt gat ggt ttt atg aac tgg tac caa cag aaa cca      192
Val Asp Tyr Asp Gly Asp Gly Phe Met Asn Trp Tyr Gln Gln Lys Pro
    50                  55                  60

gga cag cca ccc aaa ctc ctc atc tat act gca tcc aat cta gaa tct      240
Gly Gln Pro Pro Lys Leu Leu Ile Tyr Thr Ala Ser Asn Leu Glu Ser
65                  70                  75                  80

ggg atc cca gcc agg ttt agt ggc agt ggg tct ggg aca gac ttc acc      288
Gly Ile Pro Ala Arg Phe Ser Gly Ser Gly Ser Gly Thr Asp Phe Thr
                85                  90                  95

ctc aac atc cat cct gtg gag gag gag gat gct gca acc tat tac tgt      336
Leu Asn Ile His Pro Val Glu Glu Glu Asp Ala Ala Thr Tyr Tyr Cys
            100                 105                 110

cag caa agt aat gag gat ccg tgg acg ttc ggt gga ggc acc aag ctg      384
Gln Gln Ser Asn Glu Asp Pro Trp Thr Phe Gly Gly Gly Thr Lys Leu
        115                 120                 125

gaa atc aaa cgg gct gat gct gca cca act gta tcc atc ttc cca cca      432
Glu Ile Lys Arg Ala Asp Ala Ala Pro Thr Val Ser Ile Phe Pro Pro
    130                 135                 140

tcc agt gag cag tta aca tct gga ggt gcc tca gtc gtg tgc ttc ttg      480
Ser Ser Glu Gln Leu Thr Ser Gly Gly Ala Ser Val Val Cys Phe Leu
145                 150                 155                 160

aac aac ttc tac ccc aaa gac atc aat gtc aag tgg aag att gat ggc      528
Asn Asn Phe Tyr Pro Lys Asp Ile Asn Val Lys Trp Lys Ile Asp Gly
                165                 170                 175

agt gaa cga caa aat ggc gtc ctg aac agt tgg act gat cag gac agc      576
Ser Glu Arg Gln Asn Gly Val Leu Asn Ser Trp Thr Asp Gln Asp Ser
            180                 185                 190

aaa gac agc acc tac agc atg agc agc acc ctc acg ttg acc aag gac      624
Lys Asp Ser Thr Tyr Ser Met Ser Ser Thr Leu Thr Leu Thr Lys Asp
        195                 200                 205

gag tat gaa cga cat aac agc tat acc tgt gag gcc act cac aag aca      672
Glu Tyr Glu Arg His Asn Ser Tyr Thr Cys Glu Ala Thr His Lys Thr
    210                 215                 220

tca act tca ccc att gtc aag agc ttc aac agg aat gag tgt tag          717
Ser Thr Ser Pro Ile Val Lys Ser Phe Asn Arg Asn Glu Cys
225                 230                 235
```

<210> SEQ ID NO 8
<211> LENGTH: 238
<212> TYPE: PRT
<213> ORGANISM: Artificial
<220> FEATURE:
<223> OTHER INFORMATION: Synthetic Construct

<400> SEQUENCE: 8

```
Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Gly Phe Met Asn Trp Tyr Gln Gln Lys Pro
    50                  55                  60

Gly Gln Pro Pro Lys Leu Leu Ile Tyr Thr Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110
```

-continued

```
Gln Gln Ser Asn Glu Asp Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 9
<211> LENGTH: 20
<212> TYPE: PRT
<213> ORGANISM: Artificial
<220> FEATURE:
<223> OTHER INFORMATION: Epitope sequence bound by monoclonal antibody
      from hybridoma cell line 15B

<400> SEQUENCE: 9

Ile Gln Asn Leu Lys Arg Asn Ser Ser Tyr Phe Leu Gly Leu Ser Asp
1               5                   10                  15

Pro Gly Gly Arg
            20
```